US008870937B2

(12) United States Patent
Ginn et al.

(10) Patent No.: US 8,870,937 B2
(45) Date of Patent: Oct. 28, 2014

(54) METHOD FOR VESSEL ACCESS CLOSURE

(75) Inventors: Richard S. Ginn, Gilroy, CA (US); Nicanor Domingo, Santa Clara, CA (US); Hans F. Valencia, San Jose, CA (US); Robert Elliott DeCou, San Jose, CA (US); Scott Yerby, Montara, CA (US)

(73) Assignee: PROMED, Inc., Santa Clara, CA (US)

( * ) Notice: Subject to any disclaimer, the term of this patent is extended or adjusted under 35 U.S.C. 154(b) by 32 days.

(21) Appl. No.: 12/841,052

(22) Filed: Jul. 21, 2010

(65) Prior Publication Data
US 2011/0213410 A1 Sep. 1, 2011

Related U.S. Application Data

(60) Provisional application No. 61/308,859, filed on Feb. 26, 2010, provisional application No. 61/353,561, filed on Jun. 10, 2010.

(51) Int. Cl.
*A61F 2/06* (2013.01)
*A61B 17/00* (2006.01)
*A61F 2/82* (2013.01)

(52) U.S. Cl.
CPC ... *A61B 17/0057* (2013.01); *A61B 2017/00592* (2013.01); *A61B 2017/00663* (2013.01); *A61B 2017/00659* (2013.01); *A61B 2017/00597* (2013.01); *A61F 2/82* (2013.01)
USPC .......................................... 623/1.12; 606/213

(58) Field of Classification Search
USPC ......... 606/213; 623/1.1, 1.11–1.14, 1.18, 1.2, 623/1.21
See application file for complete search history.

(56) References Cited

U.S. PATENT DOCUMENTS

| 4,739,762 A | 4/1988 | Palmaz |
| 5,122,136 A | 6/1992 | Guglielmi et al. |
| 5,133,732 A | 7/1992 | Wiktor |
| 5,292,331 A | 3/1994 | Boneau |
| 5,312,360 A | 5/1994 | Behl |
| 5,350,399 A | 9/1994 | Erlebacher et al. |
| 5,421,955 A | 6/1995 | Lau et al. |
| 5,507,744 A * | 4/1996 | Tay et al. .................. 606/50 |

(Continued)

FOREIGN PATENT DOCUMENTS

| EP | 11707315.5 | 10/2012 |
| WO | 97-21403 | 6/1997 |

(Continued)

OTHER PUBLICATIONS

U.S. Appl. No. 61/251,054, filed Oct. 13, 2009.

(Continued)

*Primary Examiner* — Dianne Dornbusch
*Assistant Examiner* — Robert Lynch
(74) *Attorney, Agent, or Firm* — Sheppard Mullin Richter & Hampton LLP

(57) ABSTRACT

Embodiments are described for closing vascular access ports, such as arteriotomies, which involve placement and deployment of an expandable device configured to prevent blood flow across a subject arteriotomy while also keeping disturbance of intravascular flow to a minimum. Suitable prostheses may comprise one or more frames constructed from lengths of flexible materials, such as shape memory alloys or polymers. Such frames may be coupled to sheetlike or tubelike structures configured to spread loads, minimize thrombosis which may be related to intravascular flow, and maintain hemostasis.

26 Claims, 48 Drawing Sheets

(56) References Cited

U.S. PATENT DOCUMENTS

| | | | |
|---|---|---|---|
| 5,720,776 A | 2/1998 | Chuter et al. | |
| 5,728,133 A | 3/1998 | Kontos | |
| 5,728,134 A * | 3/1998 | Barak | 606/214 |
| 5,733,267 A | 3/1998 | Del Toro | |
| 5,873,906 A | 2/1999 | Lau et al. | |
| 6,004,329 A * | 12/1999 | Myers et al. | 606/108 |
| 6,080,182 A | 6/2000 | Shaw et al. | |
| 6,090,127 A | 7/2000 | Globerman | |
| 6,190,353 B1 | 2/2001 | Makower et al. | |
| 6,582,394 B1 | 6/2003 | Reiss et al. | |
| 6,613,070 B2 * | 9/2003 | Redmond et al. | 606/213 |
| 7,101,393 B2 | 9/2006 | Sarac | |
| 7,445,631 B2 | 11/2008 | Haug et al. | |
| 7,892,246 B2 | 2/2011 | Akin et al. | |
| 2003/0074049 A1 | 4/2003 | Hoganson et al. | |
| 2003/0100920 A1 * | 5/2003 | Akin et al. | 606/213 |
| 2004/0116848 A1 | 6/2004 | Gardeski et al. | |
| 2004/0176837 A1 | 9/2004 | Atladottir et al. | |
| 2004/0215231 A1 * | 10/2004 | Fortune et al. | 606/213 |
| 2004/0260383 A1 | 12/2004 | Stelter | |
| 2005/0085843 A1 * | 4/2005 | Opolski et al. | 606/191 |
| 2005/0125030 A1 * | 6/2005 | Forsberg et al. | 606/213 |
| 2005/0154443 A1 | 7/2005 | Linder et al. | |
| 2005/0165467 A1 | 7/2005 | Hunter et al. | |
| 2006/0100664 A1 * | 5/2006 | Pai et al. | 606/214 |
| 2006/0142842 A1 | 6/2006 | Molaei et al. | |
| 2006/0161110 A1 | 7/2006 | Lenker et al. | |
| 2006/0167537 A1 * | 7/2006 | Larsson et al. | 623/1.13 |
| 2007/0093888 A1 | 4/2007 | Thistle et al. | |
| 2007/0219610 A1 * | 9/2007 | Israel | 623/1.11 |
| 2007/0276433 A1 * | 11/2007 | Huss | 606/213 |
| 2009/0005852 A1 | 1/2009 | Gittings et al. | |
| 2009/0062841 A1 | 3/2009 | Amplatz et al. | |
| 2009/0143815 A1 | 6/2009 | Eidenschink et al. | |
| 2009/0187214 A1 | 7/2009 | Amplatz et al. | |
| 2009/0210052 A1 | 8/2009 | Forster et al. | |
| 2010/0249911 A1 | 9/2010 | Alkhatib | |
| 2011/0087270 A1 | 4/2011 | Penner et al. | |
| 2011/0213411 A1 * | 9/2011 | Ginn et al. | 606/213 |
| 2012/0065668 A1 * | 3/2012 | Ginn et al. | 606/213 |
| 2012/0083829 A1 * | 4/2012 | Ginn et al. | 606/213 |

FOREIGN PATENT DOCUMENTS

| | | |
|---|---|---|
| WO | WO00/48517 | 8/2000 |
| WO | WO2010/064244 | 6/2010 |
| WO | PCT/US2011/026335 | 3/2011 |
| WO | PCT/US2011/026335 | 5/2011 |
| WO | WO2011/067756 | 6/2011 |
| WO | WO2011/106713 A2 | 9/2011 |
| WO | PCT/US2011/026335 | 8/2012 |

OTHER PUBLICATIONS

U.S. Appl. No. 61/285,503, filed Dec. 10, 2009.

* cited by examiner

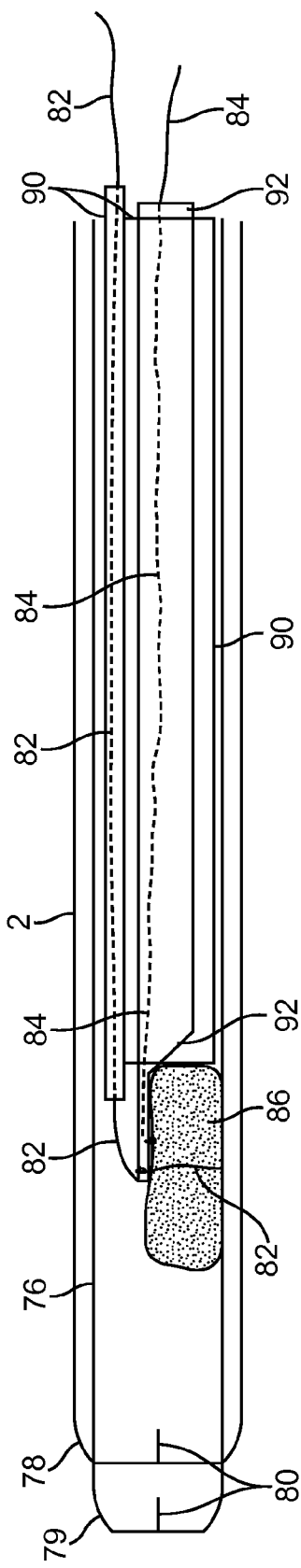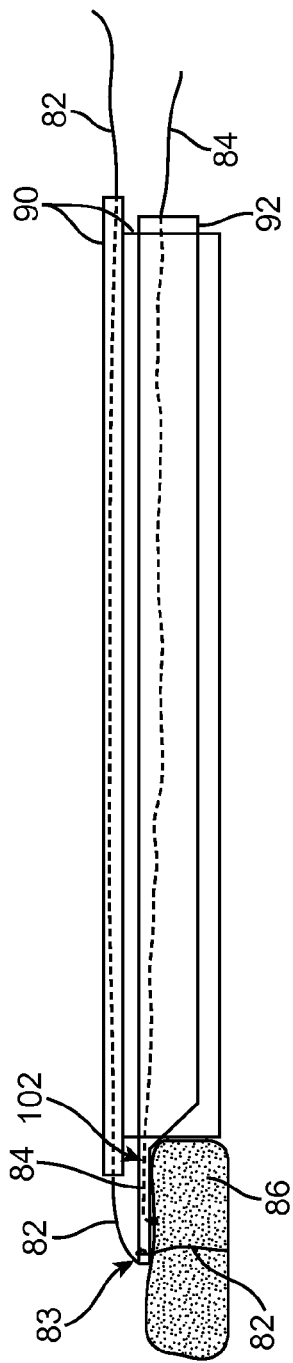
FIG. 6A
FIG. 6B

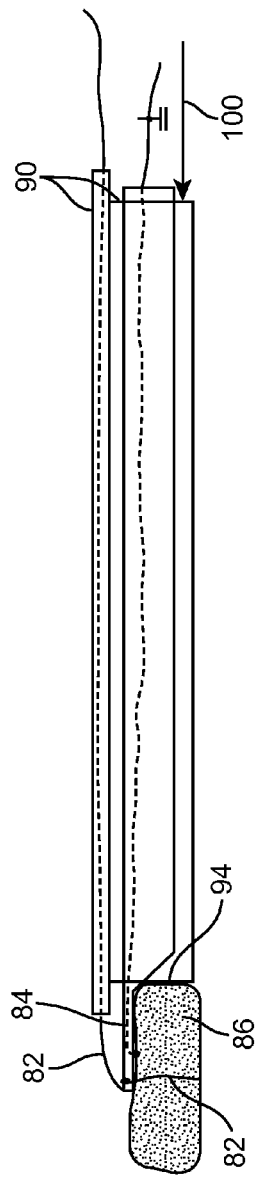
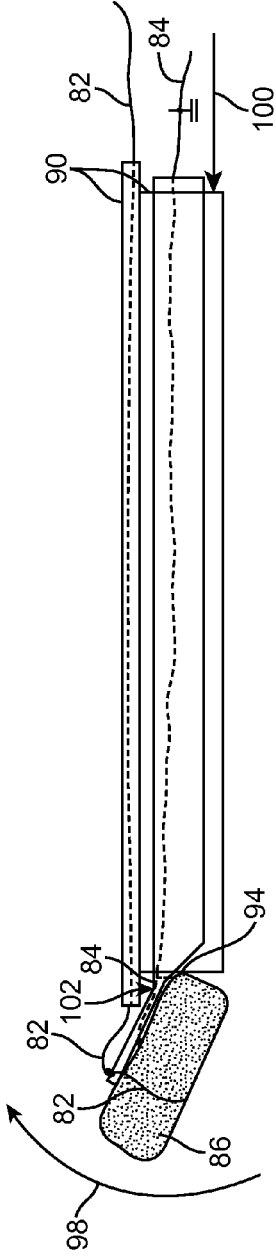
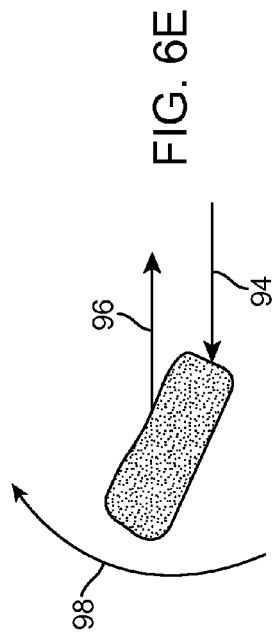
FIG. 6C
FIG. 6D
FIG. 6E

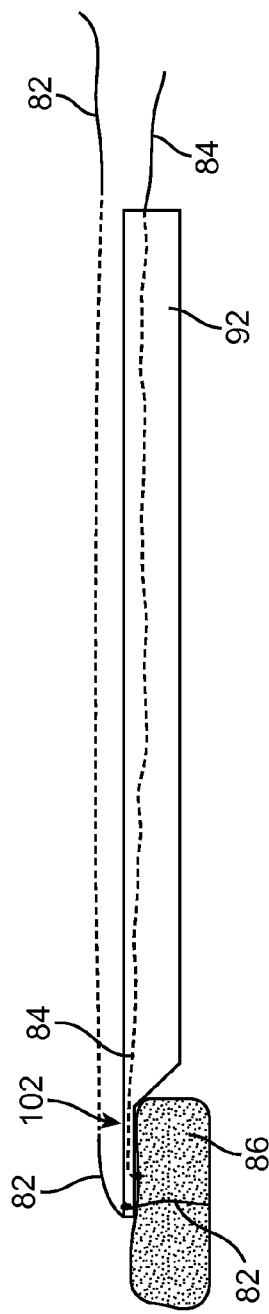
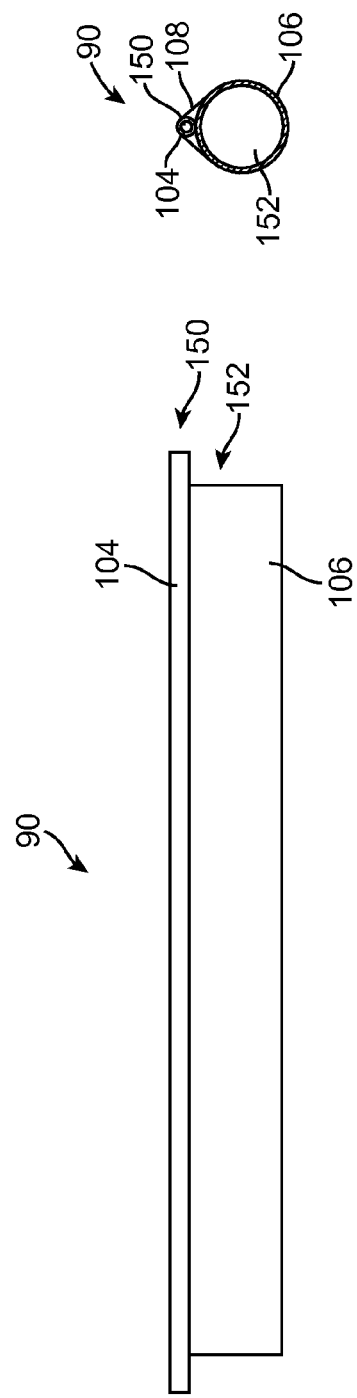
FIG. 6F
FIG. 6G
FIG. 6H

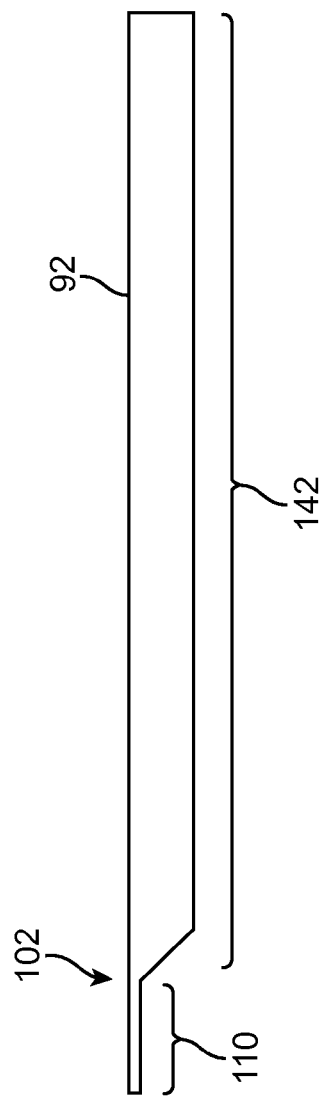
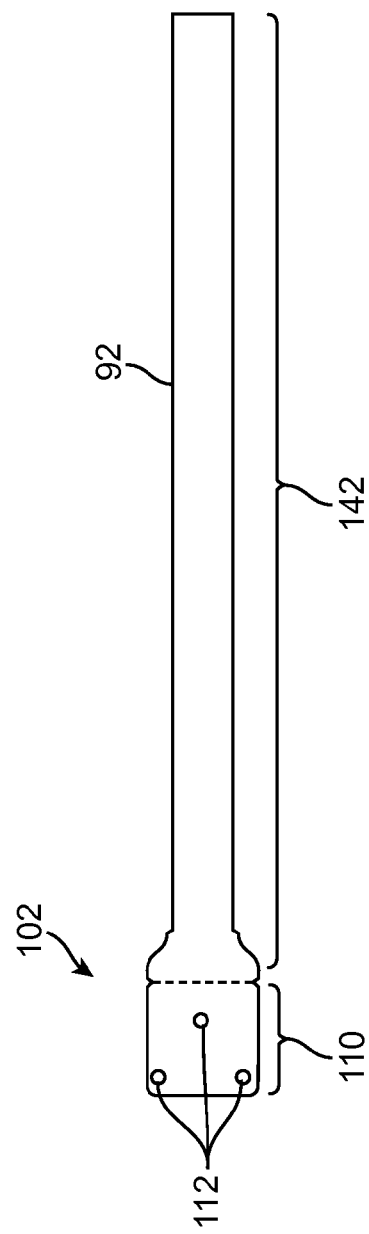

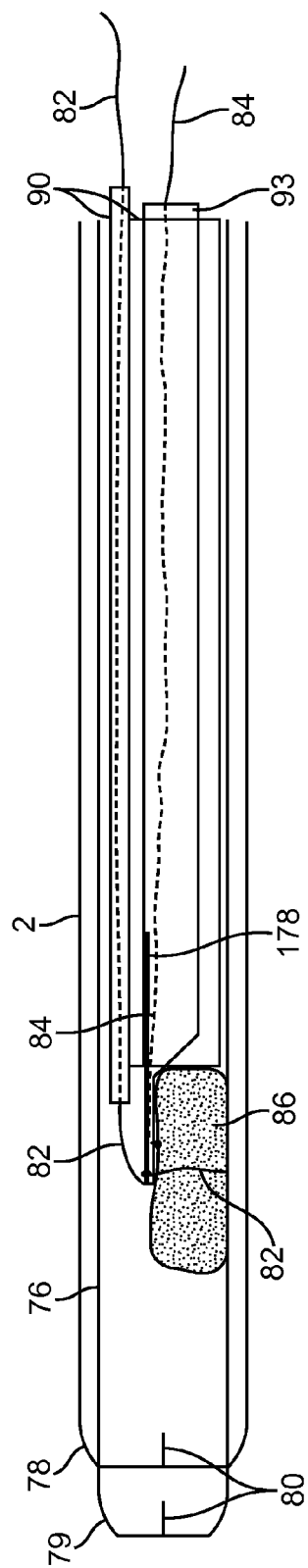
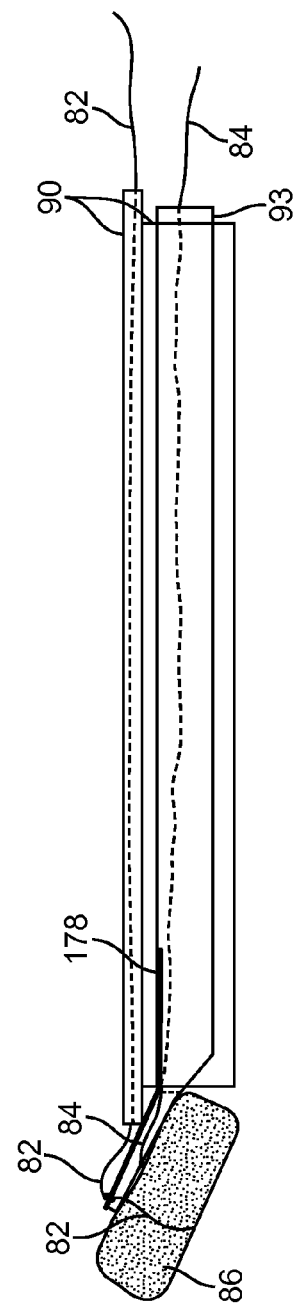
FIG. 9A
FIG. 9B

METHOD FOR VESSEL ACCESS CLOSURE

CROSS REFERENCES TO RELATED APPLICATIONS

The present application claims the benefit under 35 U.S.C. §119 to U.S. provisional patent application Ser. No. 61/308,859 filed Feb. 26, 2010, and No. 61/353,561 filed Jun. 10, 2010. The foregoing applications are hereby incorporated by reference into the present application in their entirety as if fully set forth herein.

The following copending and commonly assigned U.S. patent applications have been filed on the same day as this application. All of these applications relate to and further describe other aspects of this application and are incorporated herein by reference: U.S. patent application Ser. Nos. 12/841,083; 12/841,100; and 12/841,073; each filed Jul. 21, 2010.

FIELD OF THE INVENTION

The present invention relates generally to closure of surgically created vascular access ports or holes, such as arteriotomies, and more specifically to closure technologies pertinent to relatively large surgically-created access defects.

BACKGROUND

Minimally invasive diagnostic and interventional procedure prevalence in US and foreign hospitals continues to increase, as does the demand for certain procedures which involve placement of relatively large devices into targeted locations that are initially accessed through the vasculature. For example, percutaneous prosthetic heart valve placement and ascending aortic aneurysm stent graft procedures that are not accomplished using one or more trans-thoracic or trans-abdominal access ports generally involve one or more femoral arteriotomies which may be large in size relative to conventional femoral arteriotomies, due, at least in part, to the size of devices utilized for such procedures. Subsequent to completion of the diagnostic or interventional aspects of such treatments, any associated arteriotomies generally must be closed. While there are existing technologies for closing defects created in veins and arteries due to diagnostic and/or interventional tool access, such as those available from St. Jude Medical, Inc., Abbott Laboratories, Inc., and Access Closure, Inc. under the tradenames Angio-Seal®, StarClose®, and Mynx®, respectively, none of these are well suited for closing relatively large defects—particularly not in the arterial environment wherein relatively high flow rate and pressure are complicating factors.

BRIEF DESCRIPTION OF THE DRAWINGS

FIGS. 9A-9E illustrate various aspects of arteriotomy closure configurations wherein a collapsed closure device may be controllably rotated relative to an elongate deployment member to prevent withdrawal of the closure device through the arteriotomy.

SUMMARY

Figure 1A:
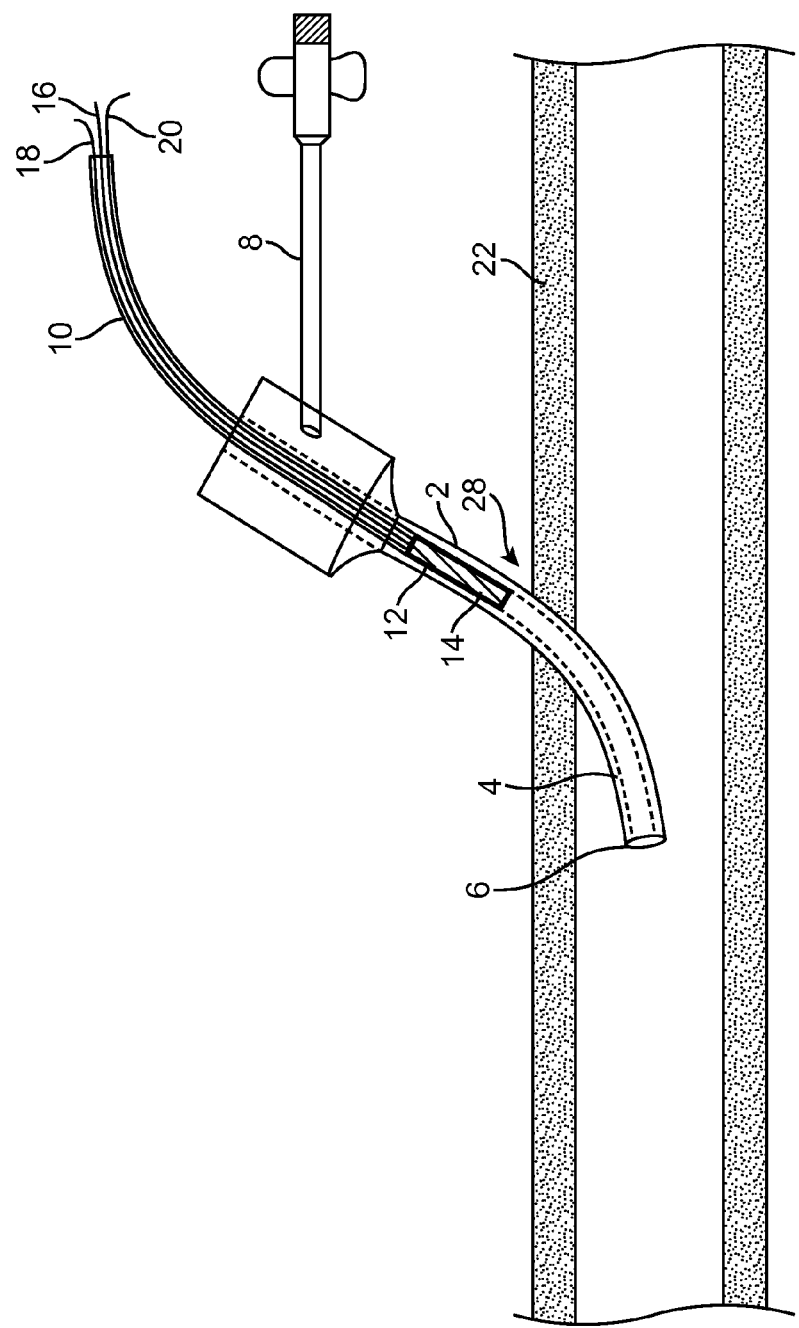
FIGS. 1A-1E illustrate aspects of an access closure device deployment wherein a collapsed device is passed through an introducer lumen to a targeted intravascular deployment position before it is deployed.

One embodiment is directed to a method of closing a hole formed in a wall of a blood vessel, comprising inserting a closure device through the hole using a deployment member to which the closure device is removably coupled; controllably moving the collapsed closure device relative to the deployment member to place the closure device into a geometric configuration selected to prevent withdrawal of the closure device back out of the hole; and decoupling the closure device from the deployment member. The method may further comprise expanding the closure device from a collapsed state to an expanded state after inserting the closure device through the hole. Controllably moving may comprise rotating the collapsed closure device relative to the deployment member to place the closure device into a rotated orientation selected to prevent withdrawal of the closure device back out of the hole when the deployment member is withdrawn. Controllably moving may comprise translating the collapsed closure device relative to the deployment member to place the closure device into compression against a portion of the deployment member. The compression may cause the collapsed closure device to controllably rotate to a rotated orientation selected to prevent withdrawal of the closure device back out of the hole when the deployment member is withdrawn. The method may further comprise applying a tensile load to a portion of the collapsed closure device to assist in moving the device to the rotated orientation. Rotating may comprise moving a restraining member relative to the closure device. The restraining member may comprise an elongate sheath defining a sheath lumen through which at least a portion of the closure device is positioned before said rotating and wherein moving comprises translating the sheath relative to the closure device. The closure device may be biased to rotate to the rotated orientation upon moving of the restraining member, and causing the closure device to rotate may comprise moving the retraining member. Rotating the collapsed closure device may comprise allowing a spring-loaded assembly to rotate the scaffold. The spring-loaded assembly may comprise an elongate bending spring member, and rotating the collapsed closure device may comprise allowing the elongate bending spring member to rotate the collapsed closure device. The spring-loaded assembly may comprise a compression spring member, and rotating the collapsed closure device may comprise allowing the compression spring member to rotate the collapsed closure device. Rotating may comprise manually manipulating an actuation assembly coupled to the deployment member. Manually manipulating may comprise loading a tensile element coupled to the closure device. Manually manipulating may comprise loading a compressive member coupled to the closure device. Decoupling may comprise pulling a tensile element that is looped around the closure device. Pulling the tensile element may untie a restraining knot tied to keep the tensile element looped around the closure device. The method may further comprise controllably expanding the scaffold from a first compressed configuration to a second expanded configuration after inserting through the hole. The closure device may be controllably expanded after it is rotated to the rotated orientation. The closure device may have proximal and distal ends and a longitudinal length in a direction parallel to a longitudinal axis of the closure device, the distal end being inserted most distally past the hole in the blood vessel, wherein the method may further comprise positioning a portion of the closure device that lies in between the proximal and distal ends of the closure device against the hole in the blood vessel after rotating the closure device to the rotated orientation. The longitudinal length of the closure device may be larger than a diameter of the hole in the blood vessel, such that after rotating the closure device to the rotated orientation, the closure device is geometrically prevented from exiting the arteriotomy. The method may further comprise tensioning a tether tensile element, which is coupled to the closure device adjacent to the position wherein the closure device may be positioned against the hole in the blood vessel, to urge the closure device against the vessel wall adjacent the hole. The method may further comprise withdrawing the deployment member and leaving behind only the closure device and tether tensile element. The method may further comprise inserting an introducer sheath defining an introducer lumen sized to accommodate insertion of the closure device and deployment member.

DETAILED DESCRIPTION

Referring again to FIG. 1A, an introducer catheter (2) is shown with its distal tip (6) inserted across a hole formed in a blood vessel, such as an arteriotomy (28), which has been created in a blood vessel such as the femoral artery (22) to provide transvascular access for a procedure such as a percutaneous heart valve installation. The hole or arteriotomy (28) may have a diameter as large as 18 French or larger. In FIG. 1A, the valve deployment related tooling has been removed, and hemostasis through the lumen (4) defined through the introducer (2) may be controlled, for example, with valves integrated into the introducer or positive flush from an associated flush assembly (8). The embodiment depicted in FIG. 1A shows a closure device assembly being inserted through the introducer to facilitate execution of a controlled arteriotomy closure, the device assembly generally comprising a collapsed closure device (14), an elongate deployment member (10) having a distal portion (12) configured to removably accommodate the collapsed device (14), an insertion/retraction member (16) removably coupled with the device (14), a deployment tension member (18) configured to cause the collapsed device (14) be expandable to a deployed or expanded shape, and an attachment tension member (20) configured to pull the device proximally toward the operator of the assembly. In one embodiment the closure device (14) may be selected to span and close an arteriotomy having a diameter as large as 18 French or larger. The elongate deployment member preferably comprises a flexible material construct, such as a polymer extrusion. The deployment and attachment tension members preferably comprise relatively small diameter sutures, wires, or tensile load bearing lines made from polymers and/or metals, such as polyethylene, polyethylene terepthalate, stainless steel, titanium, nitinol, and the like. An insertion/retraction member (16) preferably is capable of not only withstanding tensile loads, but also relatively low-level compressive loads, as in a scenario wherein such structure is utilized to push a device (14) distally. Suitable materials for an insertion/retraction member (16) include the polymers and metals mentioned above in reference to the tension members (18, 20; in construction, given the desirable compressive functionality in addition to tensile, the insertion/retraction member generally will be stiffer, and potentially larger in diameter, as compared with such tension members (18, 20). The collapsed closure device (14) may comprise a plurality of flexible structural frame elements coupled together to form a collapsible and expandable member having an outer shape that is substantially cylindrical in both collapsed form and expanded form, and defining a lumen through the cylindrical expanded form, with generally no lumen defined through the generally cylindrical collapsed form. Further description of suitable closure device (14) details is featured below.

Figure 1B:
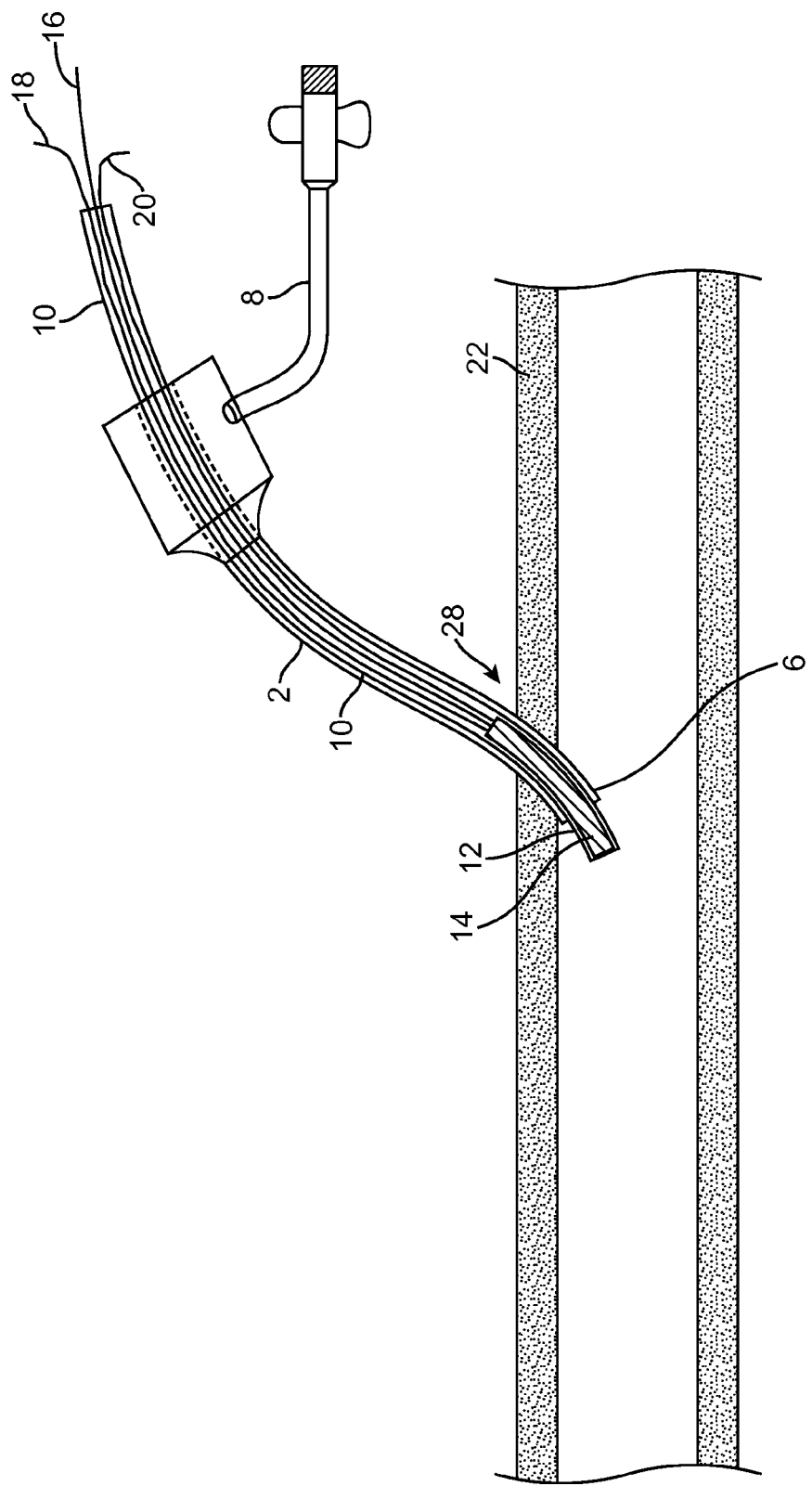

Referring to FIG. 1B, the delivery member (10) has been inserted farther through the introducer (2), and the distal portion (12) of the delivery member (10), with the collapsed device (14) confined therein, is being positioned past the distal tip of the introducer (6) and into the blood vessel (22).

Figure 1C:
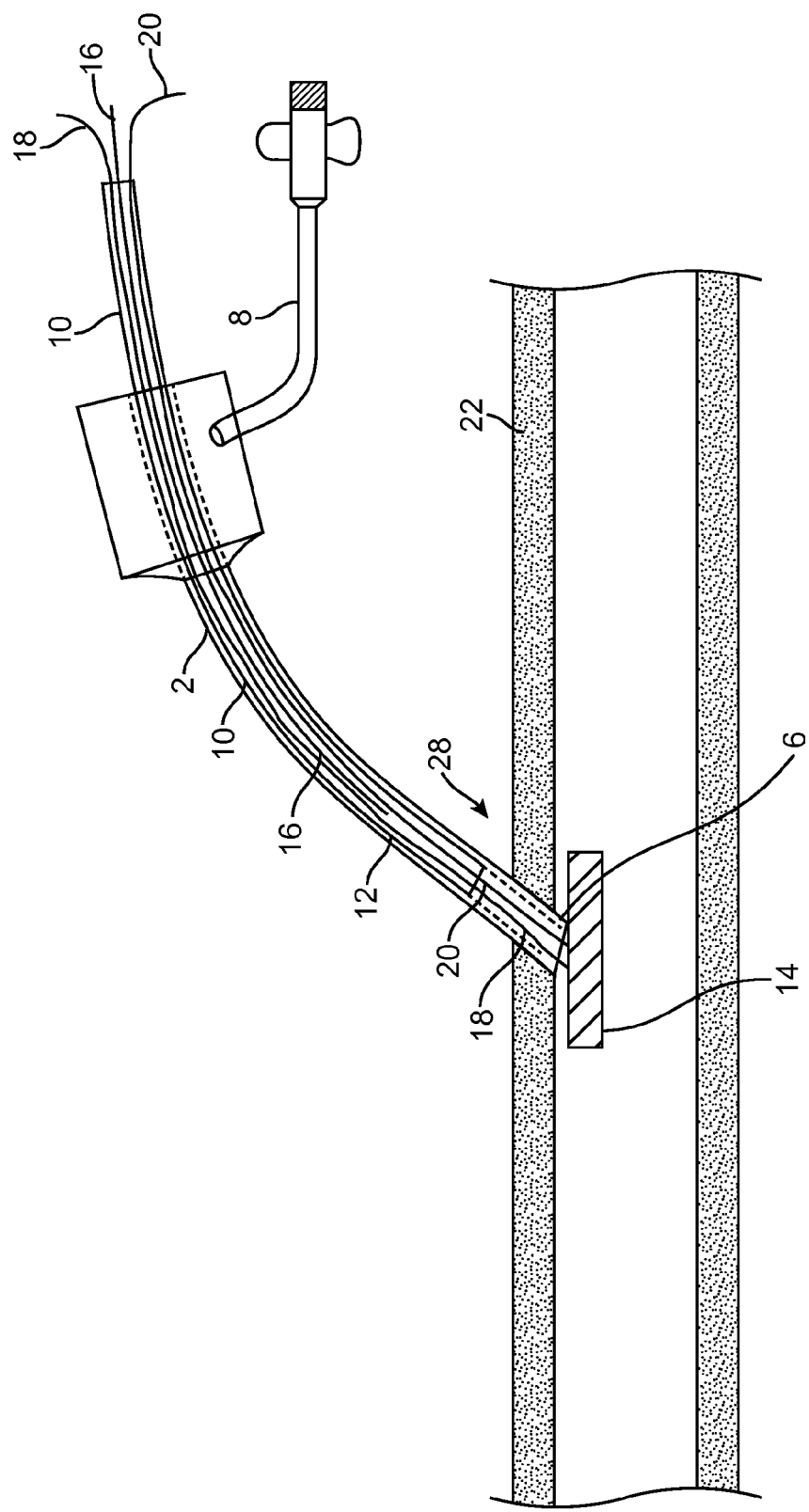

Referring to FIG. 1C, with insertion of the insertion/retraction member (16) relative to the delivery member (10), the collapsed device (14) may be pushed out of the confining distal portion (12) of the delivery member (10) and into the free bloodstream space of the vessel (22). The attachment tension member (20) may then be tensioned to maintain the collapsed device in a position adjacent to the distal tip (6) of the introducer (2) as the delivery member (10) is retracted relative to the introducer (2), as shown in FIG. 1C.

Figure 1D:
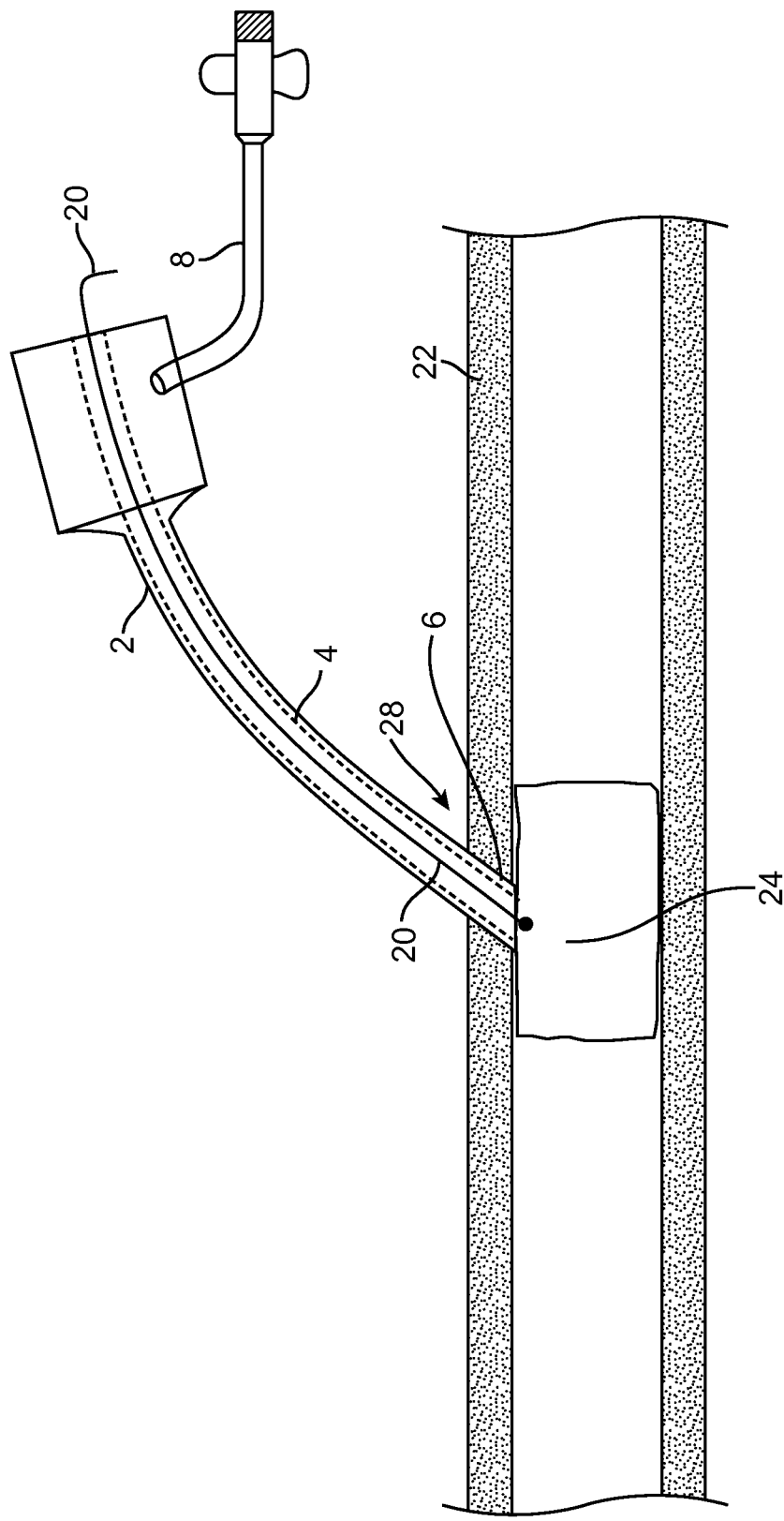

Referring to FIG. 1D, with tensioning of the deployment tension member (element 18 in FIGS. 1A-1C), the device may be allowed to expand to an expanded shape (element 24 refers to the expanded form of the previously collapsed closure device, element 14) preferably substantially occupying the entire cross section of the blood vessel (22) and spanning well beyond the diameter of the arteriotomy (28) with space on either side to prevent exit of the closure device (24) through the arteriotomy (28). The deployment tension member (18) may comprise an elongate cable, suture, string, or the like configured to occupy very little cross sectional space, and to be able to withstand tensile loading sufficient, for example, to untie a knot configured to maintain the device in a collapsed configuration. One suitable tying or knot configuration comprises what is known as a "highwayman's hitch" tied around the collapsed device (element 14 in FIGS. 1A-1C); with such a configuration, a controlled tensile pull on the deployment tension member from an operator at the proximal end of the instrument assembly causes the highwayman's hitch to untie, allowing the device to expand. Expansion from a collapsed state to an expanded state may be accomplished using a self-expanding device structure configured to expand itself to a final expanded shape, or an expandable shape configured to be expanded from a collapsed state to an expanded shape with the assistance of a balloon or other expansion device which may be placed through the device. In another embodiment, an expansion device comprising an expandable balloon or other expandable member configured to controllably expand based at least in part upon thermal energy, electric energy, shape memory, and/or hydrophilic expansion may be utilized to complete expansion of a device configuration which at least partially expands on its own, but which may require assistance to expand fully. As shown in FIG. 1D, the expanded closure device (24) remains coupled to the attachment tension member (20), and the introducer remains located adjacent to the expanded device (24), holding the arteriotomy (28) open and providing a conduit for the attachment tension member to be used to make small adjustments in the positioning of the expanded device (24) relative to the blood vessel (22) structure.

Figure 1E:
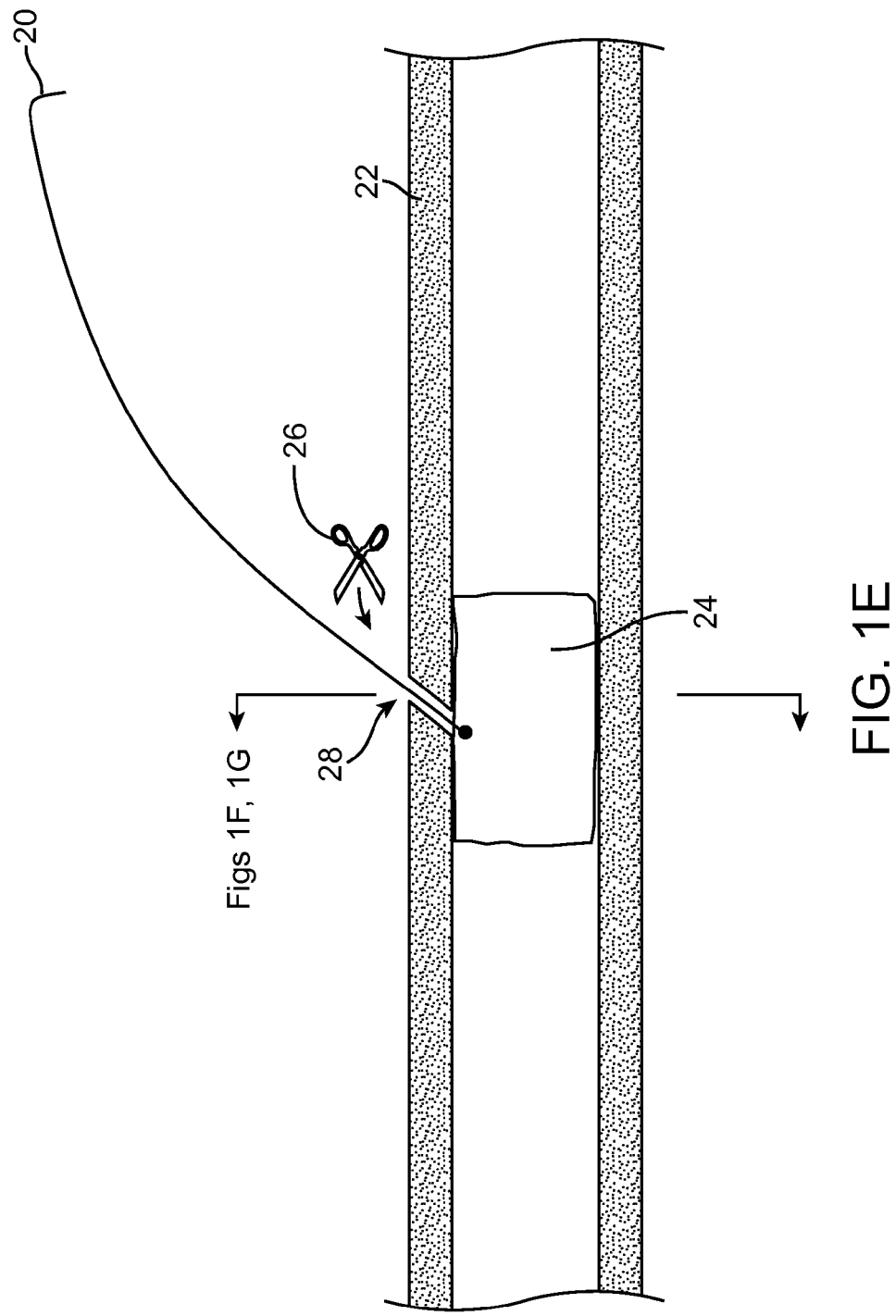

Referring to FIG. 1E, with the expanded device (24) in a desirable position, the introducer catheter (2) has been removed, allowing the arteriotomy (28) to close to a greater degree as it still surrounds the attachment tension member (20) which continues to be coupled to the expanded device (24). The attachment tension member (20) may then be released or uncoupled from the deployed device (24) with a cutting tool (26), or controlled detachment configuration, such as a small mechanical latch or fitting, or a controlled release link configuration described, for example, in U.S. Pat. No. 5,122,136, which is incorporated by reference herein in its entirety. Uncoupling of the attachment tension member (20) from the device (24) allows for the arteriotomy (28) to completely close, leaving behind an access closure supported at least in part by the expanded device.

Figure 1F:
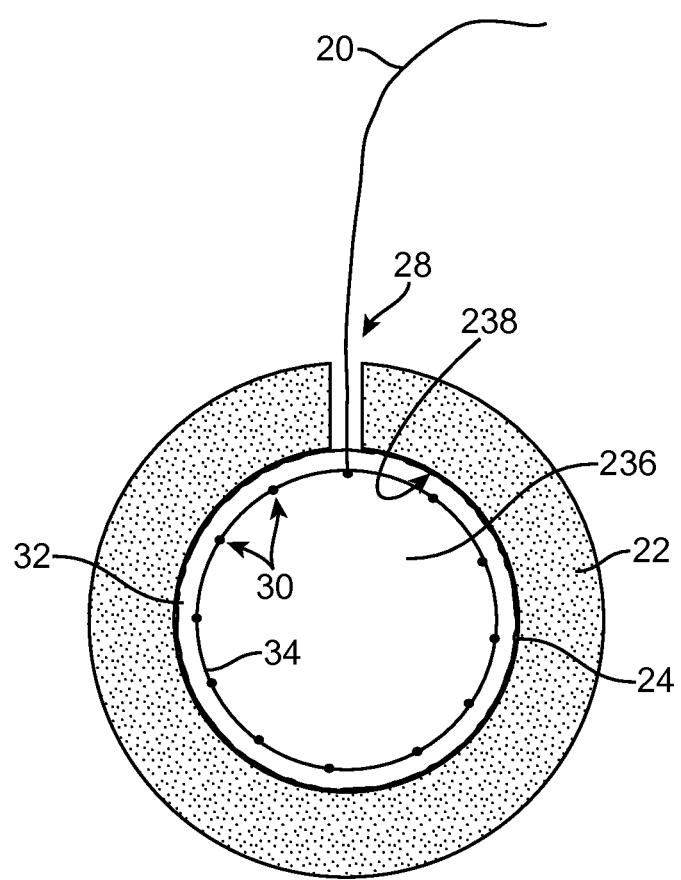
FIGS. 1F and 1G illustrate cross sectional views of two different embodiments of deployed closure device configurations.

FIG. 1F depicts a cross sectional view of the configuration illustrated in FIG. 1E. Referring to FIG. 1F, the attachment tension member (20) is shown coupled to the expanded closure device (24) and leading out of the collapsing/closing arteriotomy (28). Subsequent to decoupling of the attachment tension member (20) from the device (24), complete hemostasis of the arteriotomy may be accomplished based upon one or more of several factors: 1) the device may be configured to bias the arteriotomy closed; 2) the vessel wall tissue defining the arteriotomy therethrough generally is self-biased to close (with a somewhat spring-like state of tissue mechanics in a vessel wall, the wall is generally biased to close when mechanically allowed to do so); 3) the device (24) may comprise a structure or materials which are specifically configured to prevent the flow of blood through the wall at the location of the arteriotomy. Many suitable construction variations may be utilized for the closure device (14, 24); for example, the device embodiment depicted in FIG. 1F, comprises a frame comprised of frame elements or structural members (30) which are coupled to a thin, sheetlike connecting material (34) configured to be substantially impermeable to blood, and therefore a blocking element is pressed adjacent the arteriotomy (28) location to facilitate hemostatis across the arteriotomy (28) until it has healed shut. The outer surface of the structural member (30)/connecting material (34) assembly may be coupled to cover structure (32), and may be relatively thick (in one embodiment having a substantially uniform thickness of about 0.015 inches) as compared with the connecting material (34), which may be further selected for its ability to facilitate hemostatis of the arteriotomy (28). Suitable materials for connecting material (34) and cover structures (32) include polytetrafluoroethylene ("PTFE"), expanded polytetrafluoroethylene ("ePTFE"), polyethylene terepthalate ("PET"), polyesther, polylactic acid ("PLA"), poly glycolic acid ("PGA"), poly-lactic-co-glycolic acid, fluorinated ethylene-propylene, silicone, polyethylene, polyurethane, copolymers of any of the above, other polymers, as well as porcine or equine submucosa. The structural members (30) may comprise metals, such as nitinol, or polymers, such as resorbable polymers, as described below in reference to the construction of the collapsed (14) or expanded (24) forms of suitable closure devices.

Figure 1G:
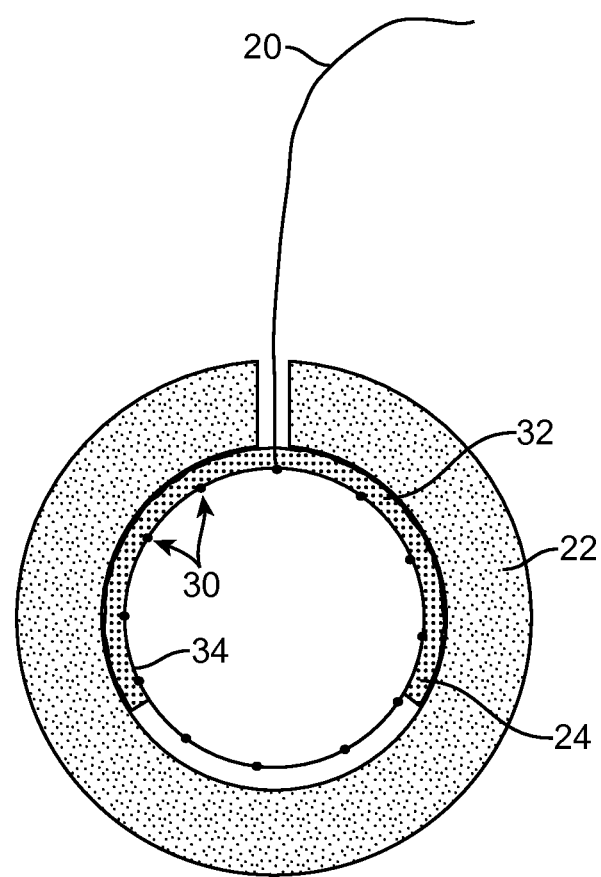
Figure 1H:
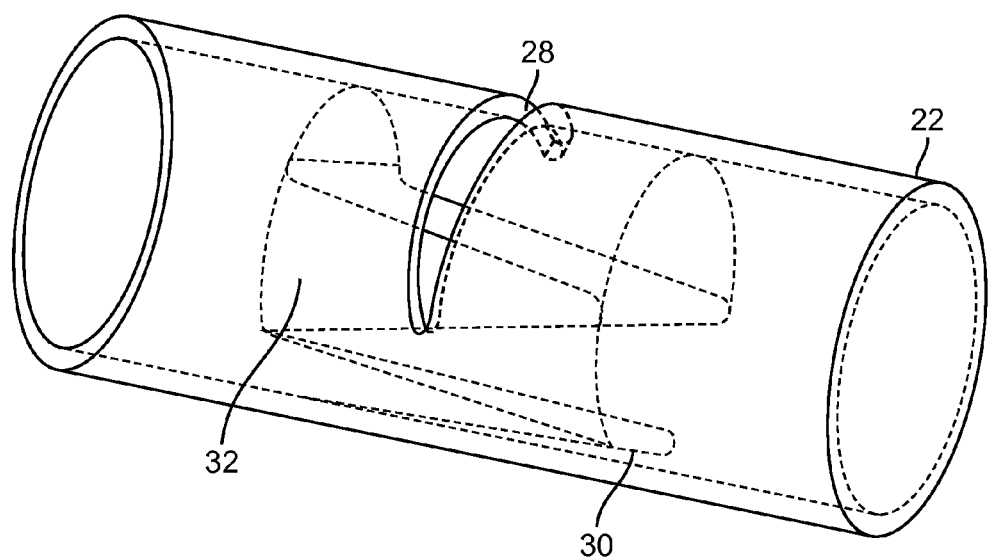
FIGS. 1H-1J illustrate orthogonal views of two different embodiments of deployed closure device configurations.

In one embodiment, a cover structure may be biased to maintain a substantially cylindrical outer surface shape, and to assist in spreading loads from the structural members (30) substantially uniformly to surrounding tissue via such substantially cylindrical outer surface shape. The closure device embodiment depicted in FIG. 1F, when in the expanded configuration as shown, forms a substantially cylindrical outer shape defining a lumen therethrough; the substantially cylindrical outer shape interfaces with substantially all (i.e., approximately 360 degrees of the circumferential inner surface 238 of the vessel 22 which defines the vessel lumen 236) of the interior surface (238) of the blood vessel (22) in the region of the arteriotomy (28), including in this embodiment, the portions of this inner surface (238) which extend along the longitudinal axis of the vessel on either side of the arteriotomy (28) for a given distance each way. In other words, if an arteriotomy is created at a position approximately midway along a two-inch-long, generally cylindrical vessel portion of interest, in one embodiment, a portion of the expanded closure device may be configured to interface with substantially all of the two-inch-long, generally cylindrical, inner surface (238). In other embodiments, an expanded closure device may be configured to interface with less than substantially all 360 degrees of this circumferential surface. For example, Referring to FIG. 1K, an embodiment is depicted that is similar to that depicted in FIG. 1F, with the exception that an expanded closure device (240) directly interfaces with approximately 90 degrees (244) of the circumferential inner surface (238) of the vessel (22). FIG. 1L depicts an embodiment wherein an expanded closure device (242) directly interfaces with approximately 135 degrees (246) of the circumferential inner surface (238) of the vessel (22). The embodiment depicted in FIG. 1G varies from that of FIG. 1F in that the cover structure (32) of FIG. 1F is configured to cover substantially the entire approximately cylindrical outer surface of the structural member (30)/connecting material (34) assembly, while the cover structure (32) of FIG. 1G is configured to cover the approximately ⅔ of the approximately cylindrical outer surface of the structural member (30)/connecting material (34) assembly closest to the arteriotomy location.

Many closure device (14) variations are suitable, with general preferred characteristics being that the device be deployable through the arteriotomy in a collapsed state, and expandable once in the targeted vessel to an expanded state which promotes closure of the hole or arteriotomy through which it was delivered. For example, in one embodiment shown in orthogonal view in FIG. 1H, the closure device may comprise a simple scaffold or frame constructed of bent and straight portions of elongate structural members (30) in a coiled, meshed, zig-zag, or other pattern coupled to a cover structure (32) positioned to promote hemostasis of the arteriotomy (28). Such structural members (30) may, for example, comprise highly flexible metallic alloys or polymeric materials, such as bioresorbable polymers. Suitable metallic alloys include nickel titanium alloys, such as the superalloy known as nitinol; other suitable materials include stainless steel, cobalt chrome, titanium, nickel, gold, tantalum, and alloys thereof. Suitable polymeric materials include those comprising poly lactic acid, poly glycolic acid, poly(lactic-co-glycolic acid), silicone, polyethylene, polyurethane, polyesther, and copolymers thereof.

Figure 1J:
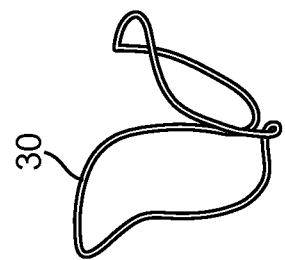
Figure 1I:
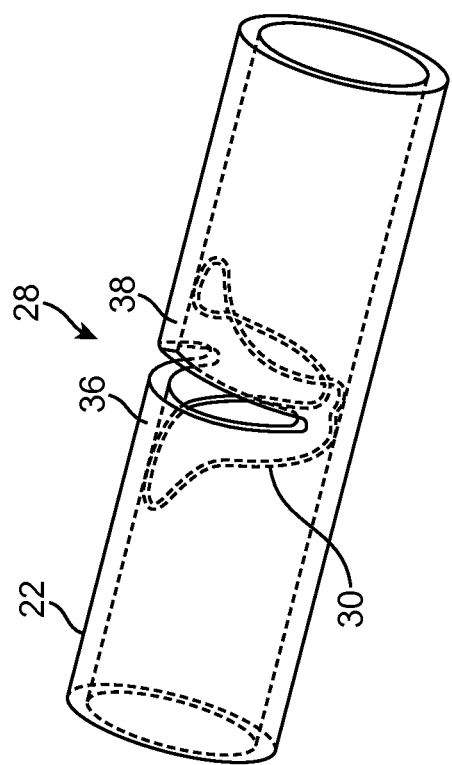
Figure 1K:
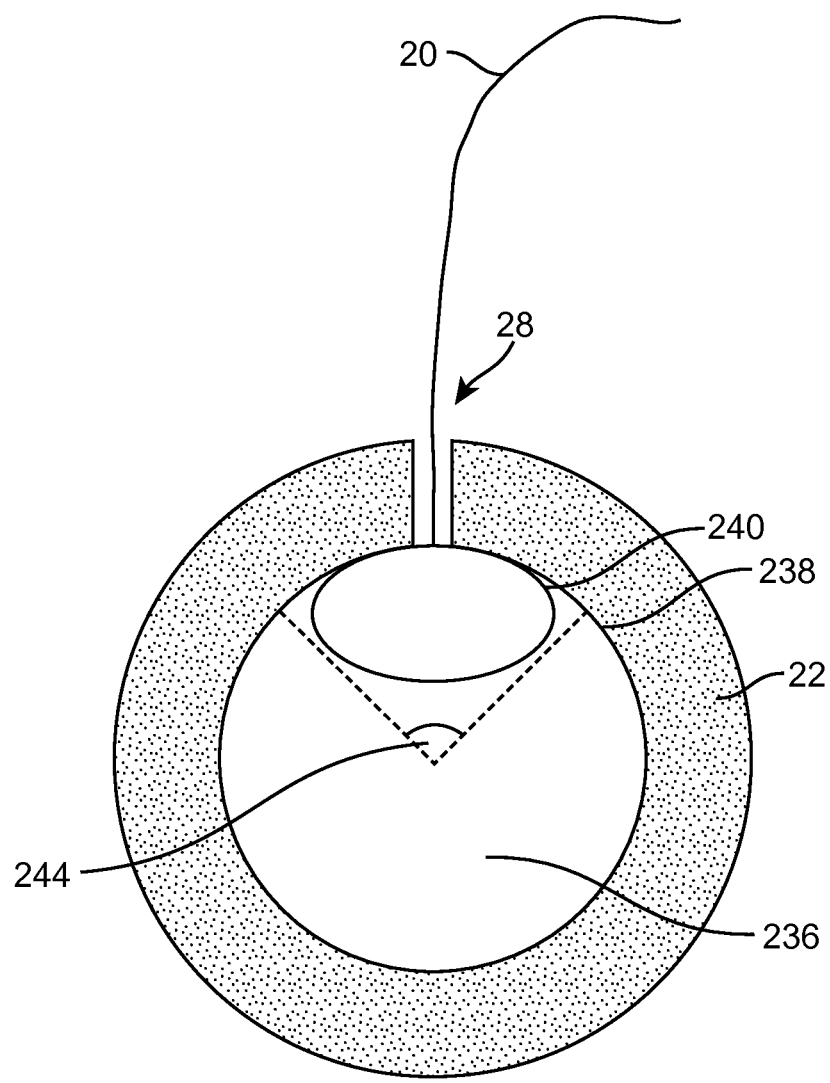
FIGS. 1K and 1L illustrate cross sectional views of two different embodiments of deployed closure device configurations.
Figure 1L:
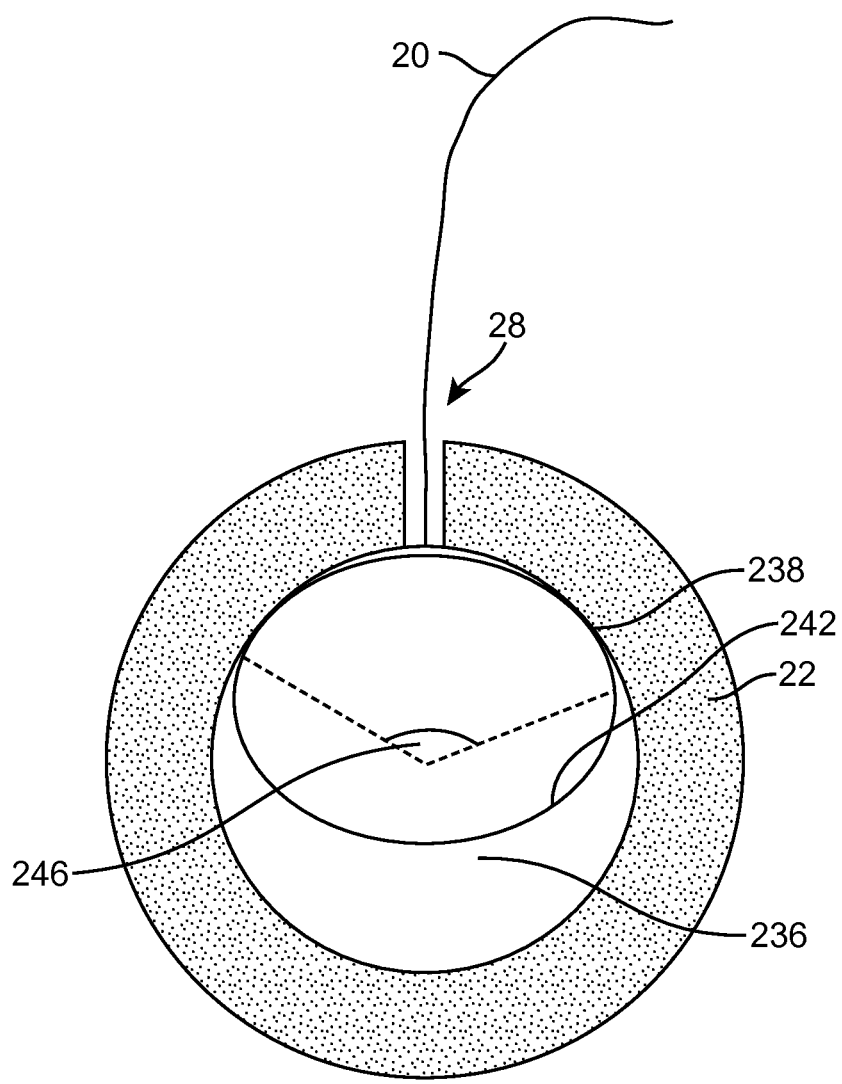

In another embodiment, such as that shown in FIGS. 1I and 1J, a suitable closure device (14) may comprise merely a scaffold or frame comprising bent and/or straight portions of elongate structural member (30) material in a configuration that tends to bias an arteriotomy (28) closed when in a deployed/expanded configuration by urging adjacent vessel (22) wall tissue portions (36, 38) toward each other by means of small hooks, or high-friction or protein binding materials that are configured to attach or adhere to the inside of the vessel wall.

In another embodiment, a closure device (14) may comprise an expandable scaffold or frame such as an intraluminal stent or stentlike structure. The stent may be self-expanding or balloon-expandable and may be a stent configured for any blood vessel including coronary arteries and peripheral arteries (e.g., renal, Superficial Femoral, Carotid, and the like), a urethral stent, a biliary stent, a tracheal stent, a gastrointestinal stent, or an esophageal stent, for example. More specifically, the stent may be, for example, a stent available commercially as a Wallstent, Palmaz-Shatz, Wiktor, Strecker, Cordis, AVE Micro Stent, Igaki-Tamai, Millenium Stent (Sahajanand Medical Technologies), Steeplechaser stent (Johnson & Johnson), Cypher (Johnson & Johnson), Sonic (Johnson & Johnson), BX Velocity (Johnson & Johnson), Flexmaster (JOMED) JoStent (JOMED), S7 Driver (Medtronic), R-Stent (Orbus), Tecnic stent (Sorin Biomedica), BiodivYsio (Biocompatibles Cardiovascular), Trimaxx (Abbott), DuraFlex (Avantec Vascular), NIR stent (Boston Scientific), Express 2 stent (Boston Scientific), Liberte stent (Boston Scientific), Achieve (Cook/Guidant), S-Stent (Guidant), Vision (Guidant), Multi-Link Tetra (Guidant), Multi-Link Penta (Guidant), Multi-Link Vision (Guidant), Gianturco-Roubin FLEX-STENT®, GRII™, SUPRA-G, or V FLEX coronary stents from Cook Inc. (Bloomington, Ind.). Some exemplary stents are also disclosed in U.S. Pat. No. 5,292,331 to Boneau, U.S. Pat. No. 6,090,127 to Globerman, U.S. Pat. No. 5,133,732 to Wiktor, U.S. Pat. No. 4,739,762 to Palmaz, and U.S. Pat. No. 5,421,955 to Lau, each of which is incorporated by reference herein in its entirety. Suitable expandable stentlike structures are also disclosed in percutaneous valve configuration disclosures. For example, the configuration disclosed in U.S. Pat. No. 7,445,631 to Sadra Medical, Inc., absent the valve leaflets, may be suitably used in the subject application; U.S. publication 2009/0210052 to Forster et al discloses (for example, FIGS. 2A-2C) a tri-star collapsible frame configuration which may be utilized absent the valve leaflets in the subject application; each of these references is incorporated by reference herein in its entirety.

Any of the above devices, scaffolds, frames, stents, or stentlike structures may be combined with strips, sheets, or sheetlike portions of connecting material, such as PTFE or ePTFE, to form what may be referred to as a variant of a stent graft. A suitable stent graft is described, for example, in PCT Publication WO 1997-021403 to Prograft Medical, and is incorporated by reference herein in its entirety. Further, any of the aforementioned frames may be coupled to a cover structure (with or without connecting material as well) comprising a metal or polymer material positioned to assist in maintaining hemostasis of the arteriotomy, as depicted in FIGS. 1F-1H.

Figure 2A:
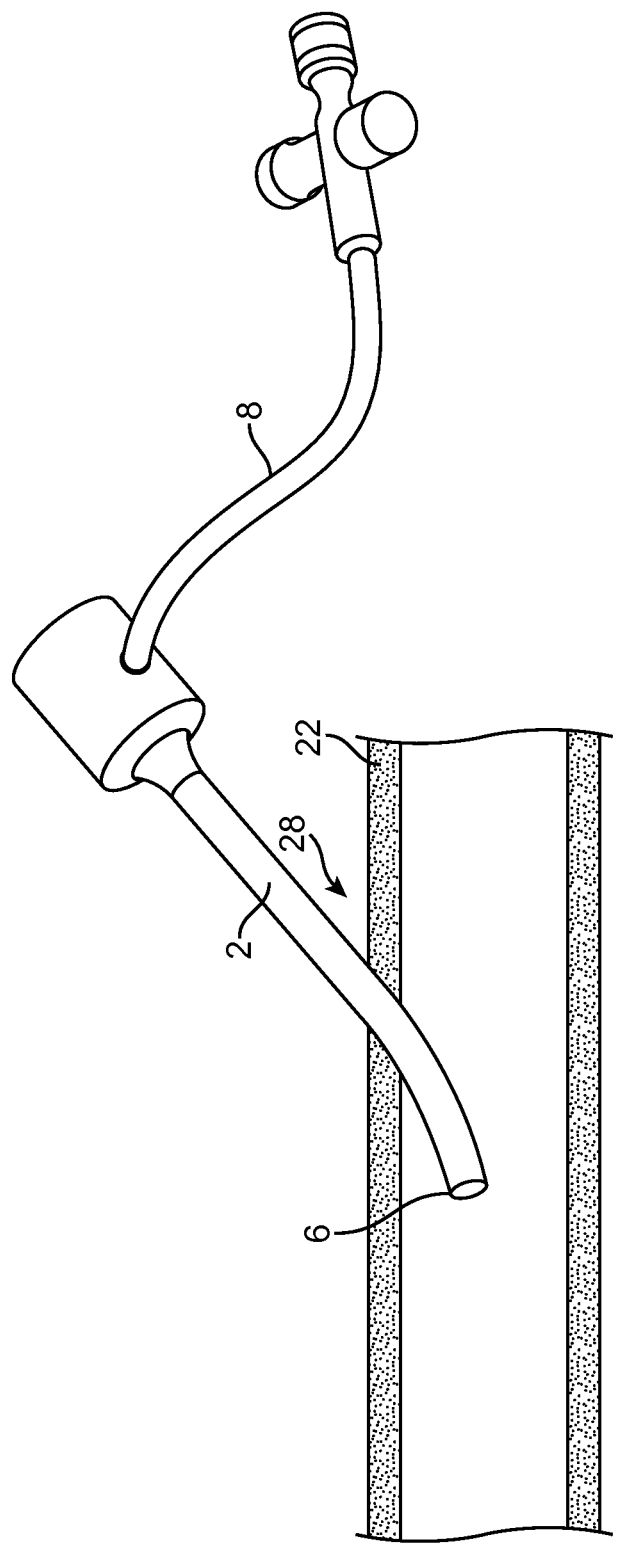
FIGS. 2A-2F illustrate aspects of an access closure device deployment wherein a two-portion collapsed device is passed through an introducer lumen to a targeted intravascular deployment position before expansion.
Figure 2B:
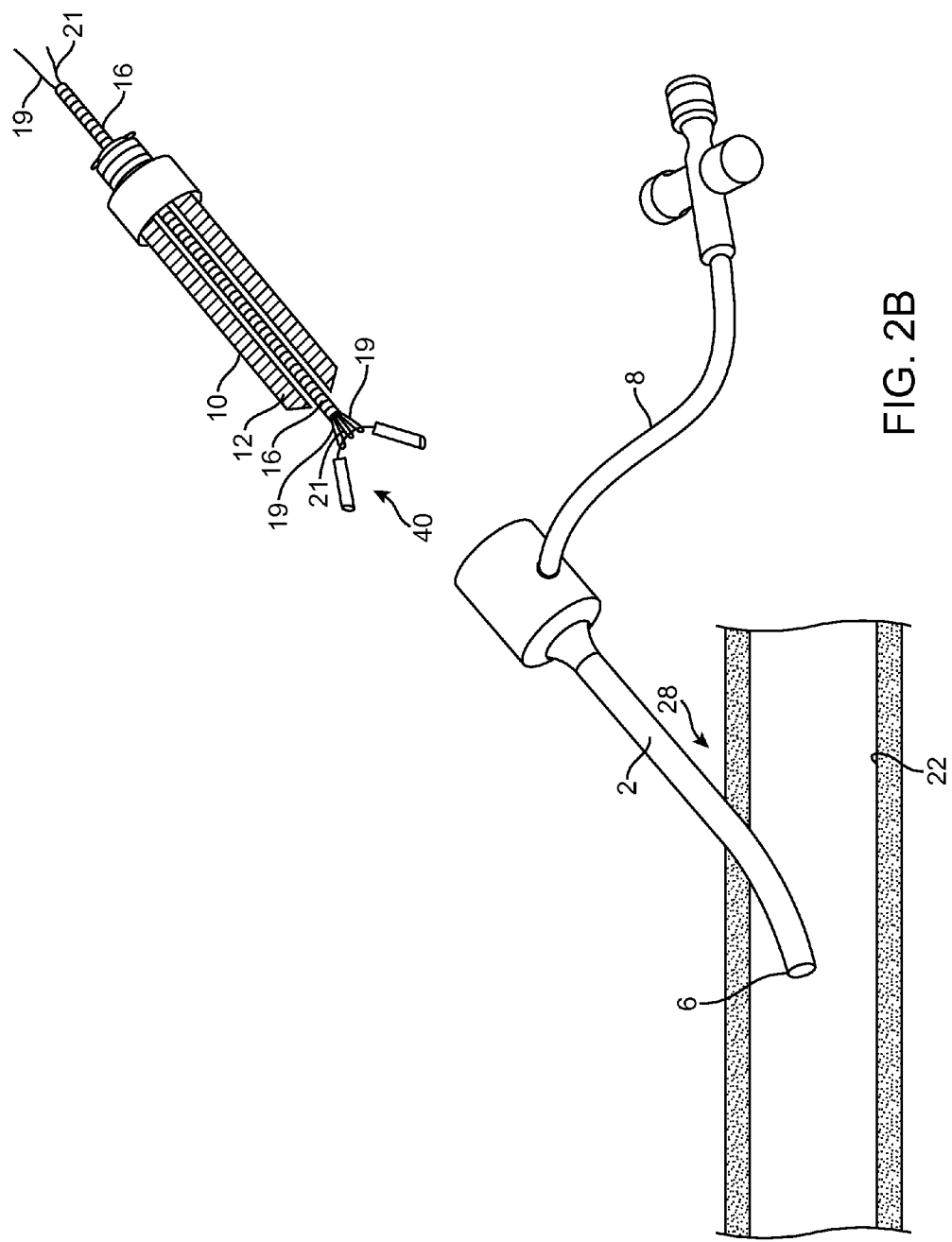

Referring to FIG. 2A-2I, another embodiment is depicted wherein a closure device (40) has two end portions coupled by a highly bendable midportion. Referring to FIG. 2A, a distal tip (6) of an introducer catheter (2) is positioned through an arteriotomy (28) formed in a blood vessel (22). In one embodiment, the arteriotomy may be as large as 18 French or larger in diameter. An access closure device deployment assembly is shown being advanced toward the introducer (2) in FIG. 2B, the assembly comprising an expandable device (40) removably coupled to a deployment tension member (19) and an attachment tension member (21), each of which are movably coupled through a device insertion/retraction member (16) to a proximal location where they may be manipulated or controlled by an operator.

Figure 2C:
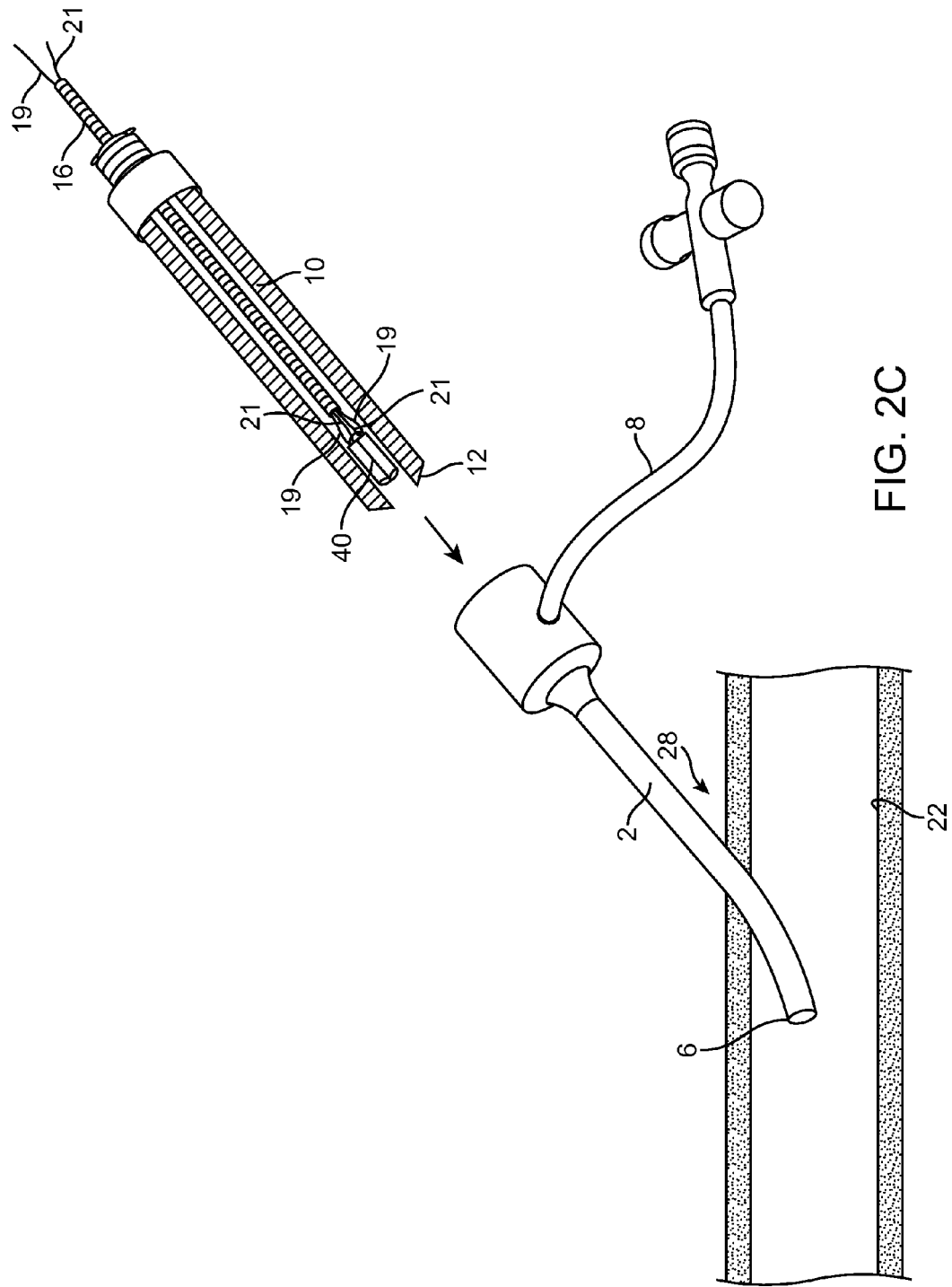
Figure 2D:
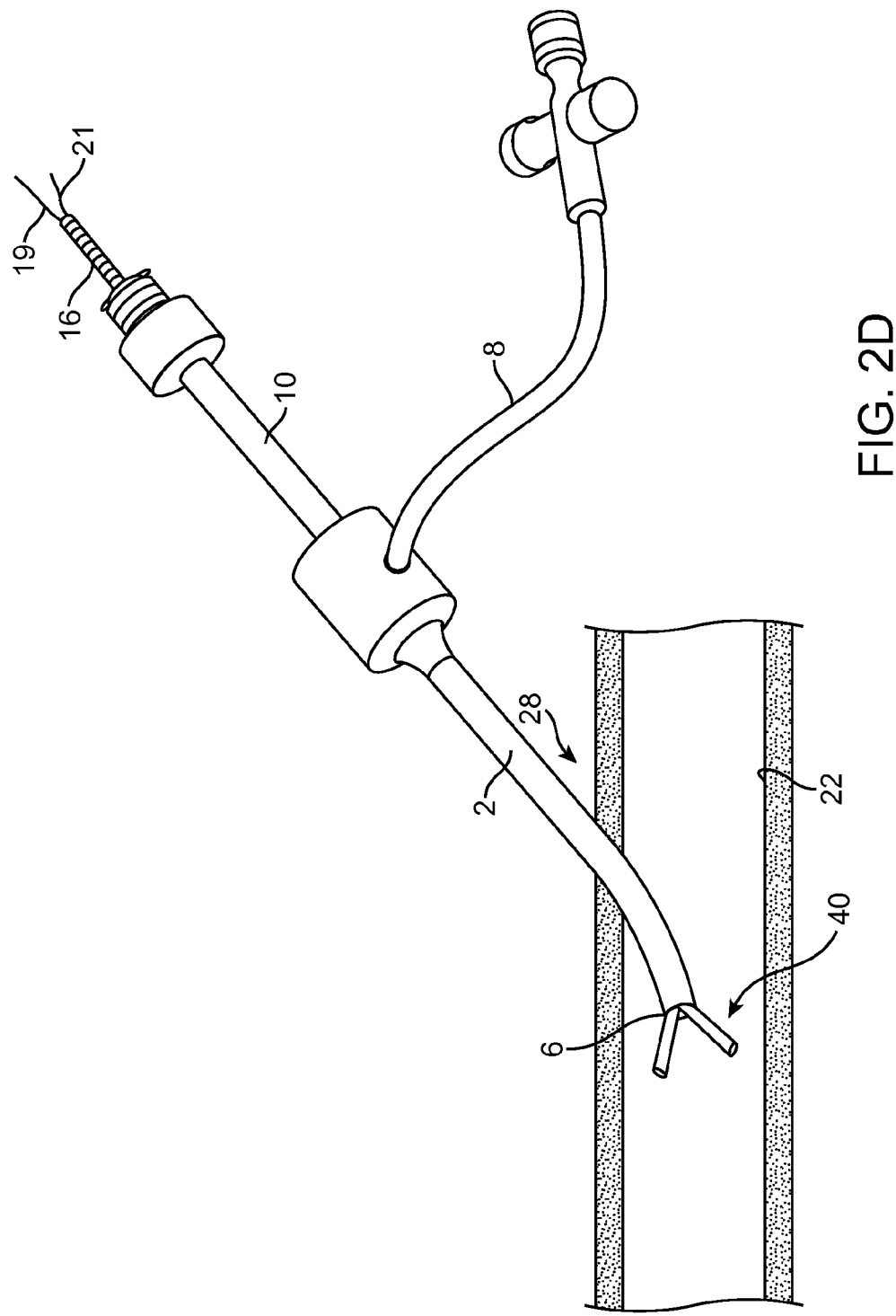
Figure 2E:
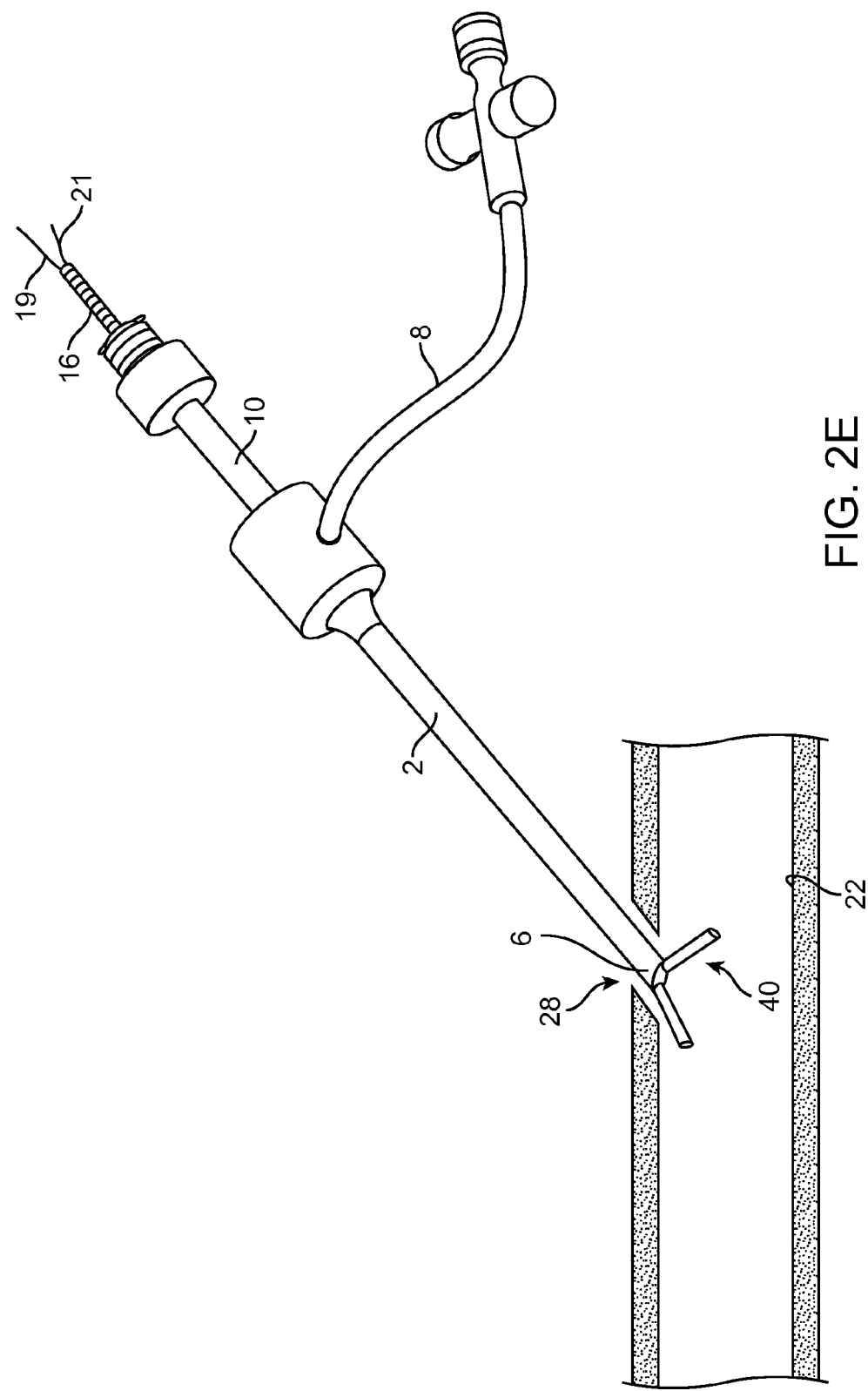
Figure 2F:
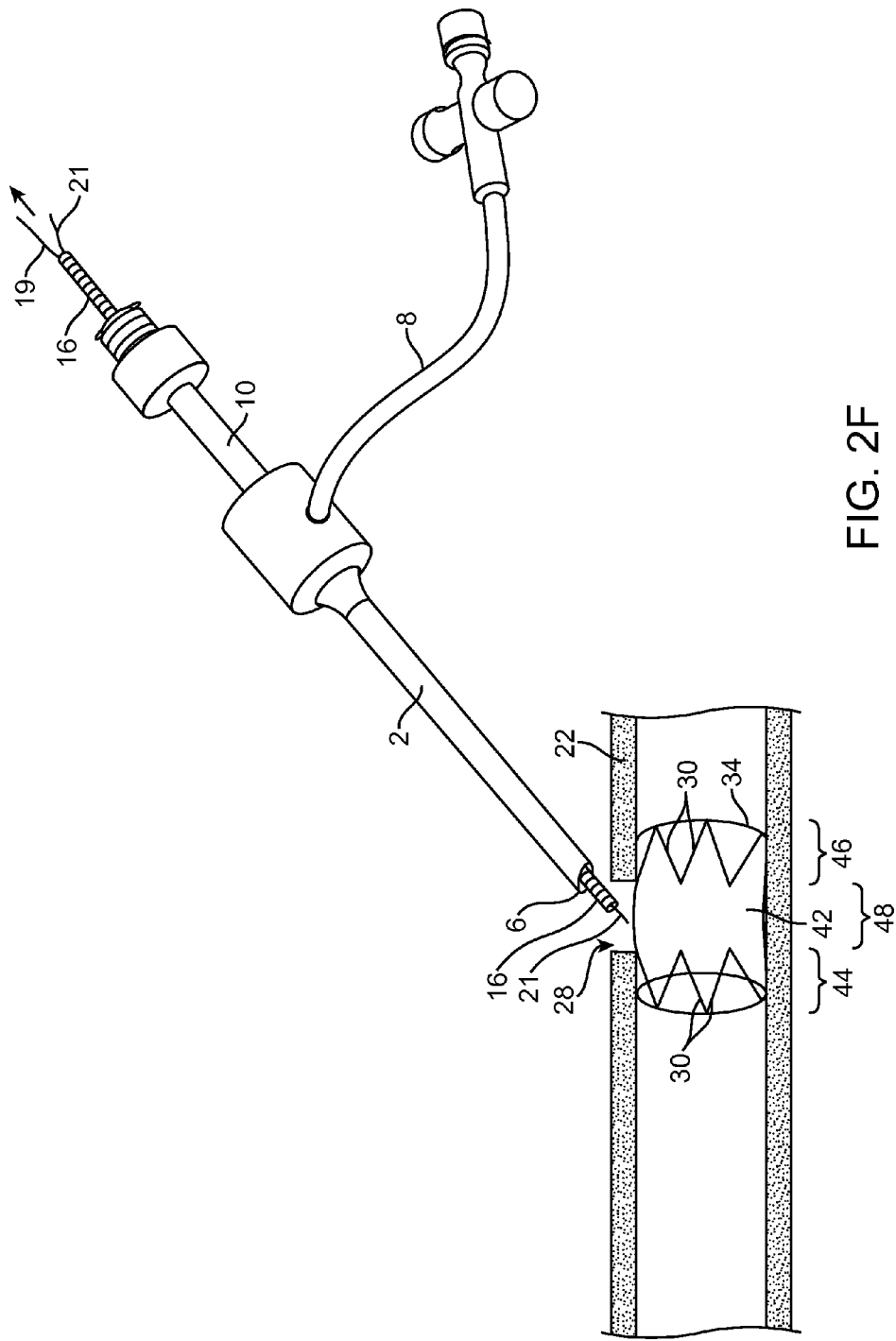
Figure 2I:
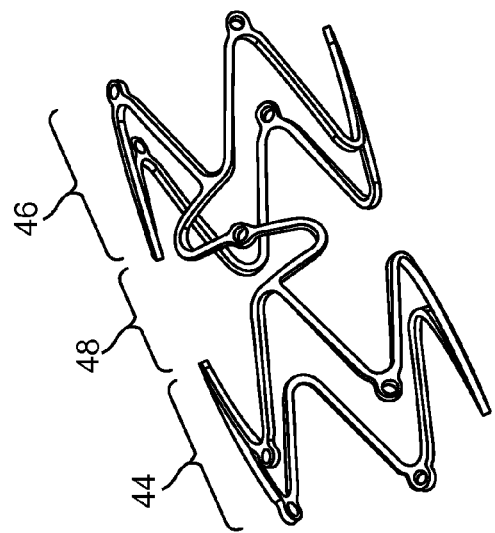
FIGS. 2G-2I illustrate side views and an orthogonal view, respectively, of a suitable device frame configuration.
Figure 2H:
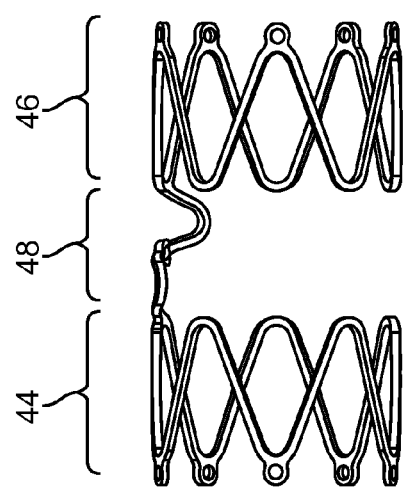
Figure 2G:
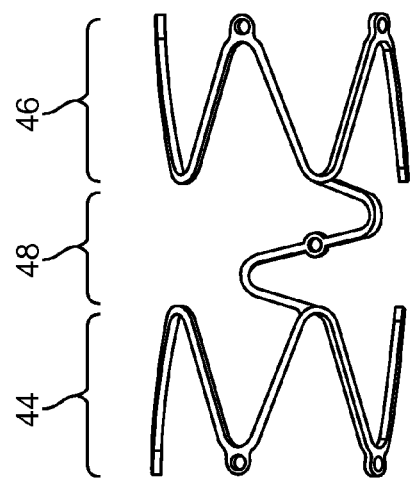

Referring to FIG. 2C, the insertion/retraction member (16) is withdrawn relative to a delivery member (10), causing the collapsed device (40) to become disposed within the distal portion (12) of the delivery member (10). Such a configuration may be inserted into the introducer catheter (2), as shown in FIG. 2D, to dispose the collapsed device (40) past the distal tip (6) of the introducer (2). Referring to FIG. 2E, the introducer (2) may be withdrawn to urge the collapsed device (40) into a position wherein it is approximately centered adjacent the arteriotomy (28) to provide a temporarily hemostasis through the arteriotomy (28). Referring to FIG. 2F, having placed the non-expanded device (40) in a desirable position as in FIG. 2E, the deployment tension member (19) may be proximally tensioned to allow the device to expand, such as by using a highwayman's hitch as described above, and the attachment tension member (21) may be subsequently uncoupled from the expanded device (42) to allow for the arteriotomy (28) to close and for the delivery instrumentation to be removed. As shown in FIG. 2F, for example, the deployed device (42) spans across the longitudinal length of the arteriotomy (28) with extra length on both sides to provide stability and leak prevention. Referring to FIGS. 2G-2I, three views of a suitable structural member frame for the deployment paradigm illustrated in FIGS. 2A-2F are depicted to show that two substantially cylindrical end portions (44, 46) are coupled by a highly flexible mid portion (48) in this embodiment, the midportion (48) preferably being positioned directly adjacent the arteriotomy location to provide support for the closure (i.e., by urging a related cover member directly against the arteriotomy location); such preferred position/orientation of the flexible mid portion (48) may be accomplished, at least in part, by interfacing a tensile member (not shown) directly with the midportion (48), for example by tying with a knot to one of the small apertures shown in the midportion (48) embodiments of FIGS. 2G-2I. Tension on such a tensile member is likely to assist with the orientation/position selection described herein, either before or after allowing the device to reach its expanded state. Such structural members may comprise materials similar to the structural members (30) described in reference to FIGS. 1A-1J, and may be coupled to sheetlike members and/or cover members for form a substantially cylindrical expanded device surface shape (as in the embodiment shown in FIG. 2F wherein a cover member 30 extends around each of, and between (i.e., across the midportion 48 span), the two zig zag cylindrical frame sub-portions 44, 46, to span the arteriotomy 28 and play a key role in effecting the closure thereof), which also may be similar to those (34, 32) described above in reference to FIGS. 1A-1J. In other words, the embodiment shown in FIGS. 2A-2F, while delivered in a two-lobed collapsed form, may be expanded to form a substantially cylindrical shape due to a sheetlike member coupled across the frame, and/or a cover member extended across the outer surfaces of the frame.

Figure 3A:
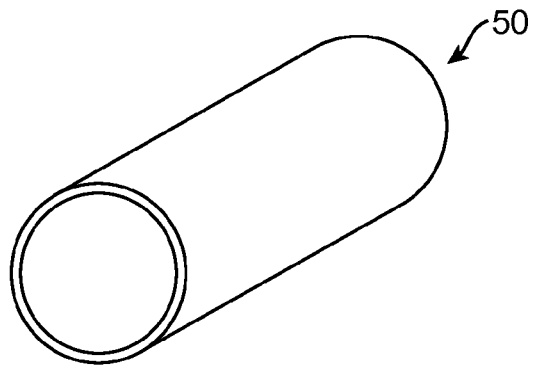
FIGS. 3A-3D illustrate orthogonal views of a device embodiment that may be rolled up into a collapsed shape, and unrolled or unfurled to an expanded shape.
Figure 3B:
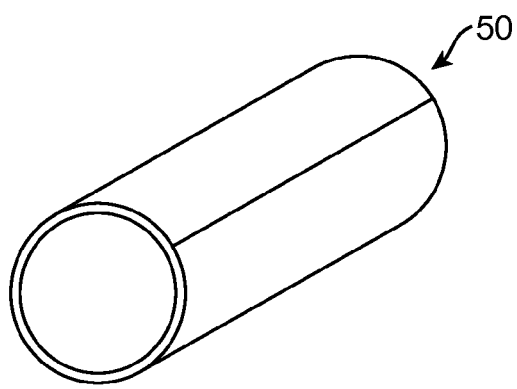
Figure 3C:
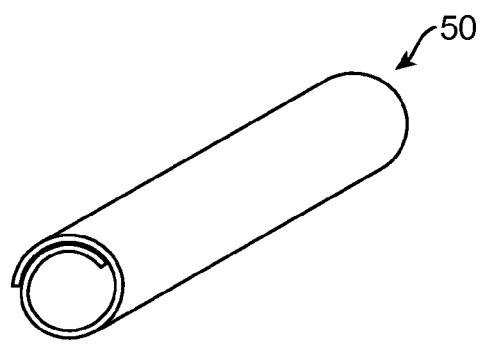
Figure 3D:
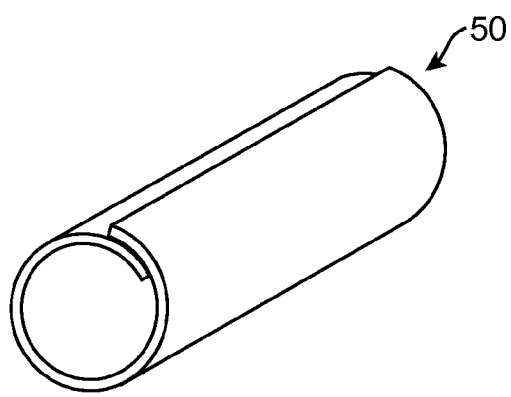

Referring to FIGS. 3A-3D, a roll-up type expandable device (50) configuration is depicted to illustrate that suitable prostheses need not be conventionally radially expandable—they may be expanded by allowing or mechanically facilitating (i.e., with an assisting device such as a balloon or unrolling torque tool), the unrolling or unfurling of a device that has been rolled into a smaller radial configuration, as illustrated in FIG. 3C.

Figure 4:
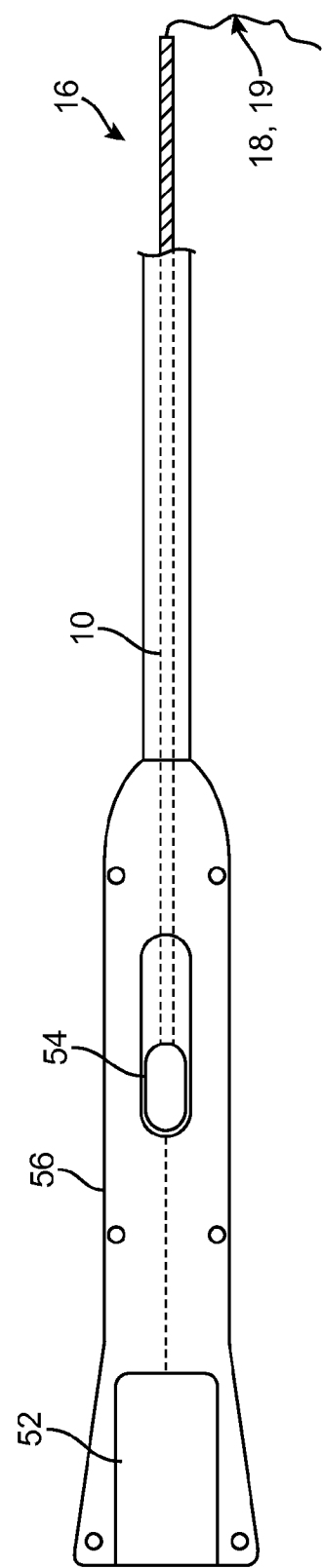
FIG. 4 illustrates one embodiment of a manual operational interface configuration.

Referring to FIG. 4, one embodiment of a handle is depicted for deploying and actuating configurations such as those described in reference to FIGS. 1A-1J and 2A-I. As shown in FIG. 4, an actuator handle body (56) is movably coupled to a delivery member (16) insertion/retraction actuator slide button (54) and a deployment tension member (18, 19) tension actuation pull feature (52). Such a configuration allows for an operator to hold the handle body (56) in one hand and easily control insertion and retraction of the insertion/retraction member (16) with a thumb or finger of the same hand, while also allowing for the operator to use fingers of the other hand to pull the deployment tension member (18, 19) tension actuation pull feature (52) and allow a related device to expand or be expanded.

Figure 5:
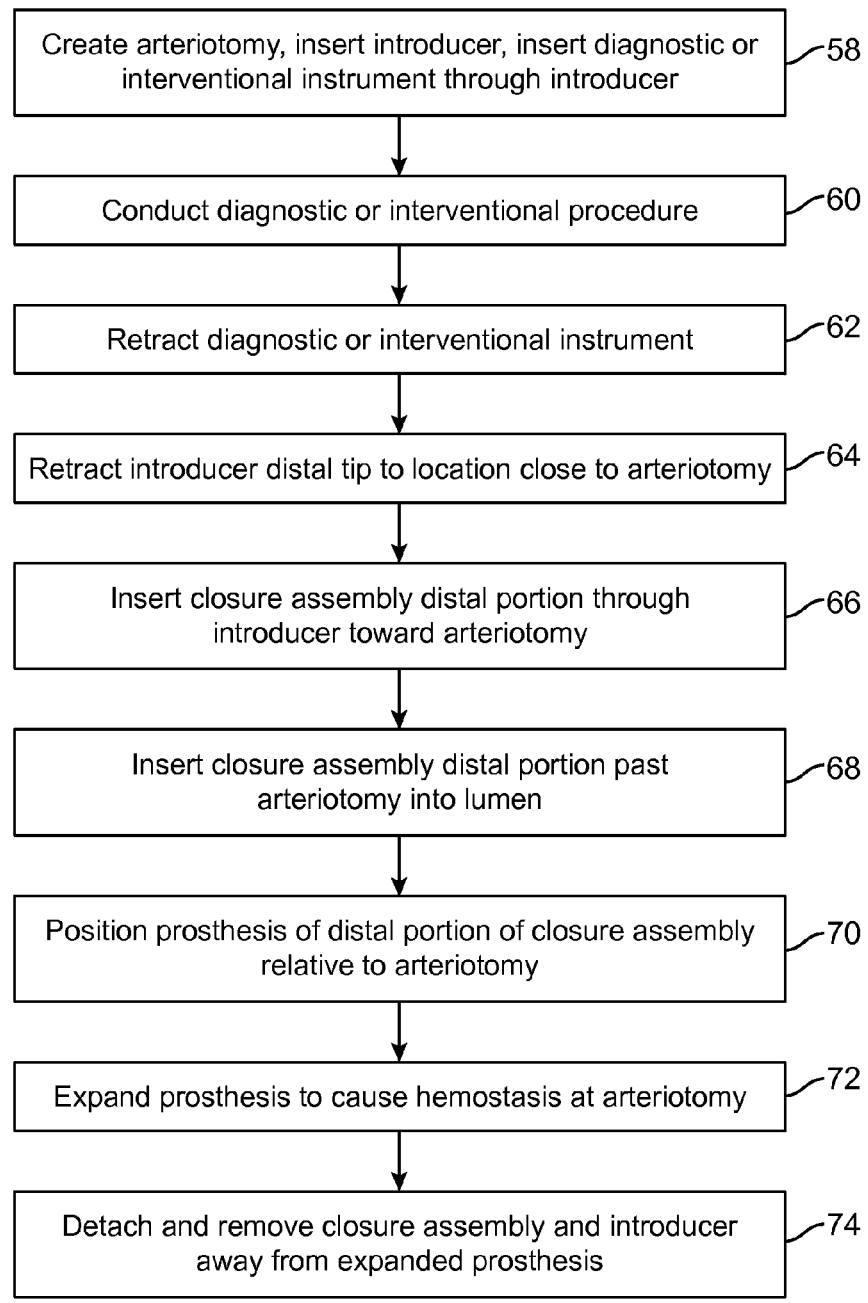
FIG. 5 illustrates various aspects of an arteriotomy closure method in accordance with the present invention.

Referring to FIG. 5, a method is illustrated wherein an arteriotomy is created, an introducer inserted, and a diagnostic or interventional tool inserted through the introducer (58) to conduct a cardiovascular procedure (60) such as a percutaneous valve replacement. After the diagnostic and/or interventional tool or tools have been retracted back through the introducer (62), it may be desirable to close the arteriotomy. A distal tip or portion of the introducer may be retracted to a position close to the arteriotomy (64) but still within the vessel, and a closure assembly comprising an expandable device configured to facilitate hemostatic of the arteriotomy may be inserted through the introducer toward the arteriotomy (66). The closure assembly distal portion may be inserted past the arteriotomy and into the vascular lumen (68), after which the device may be positioned and/or repositioned to a desired location relative to the arteriotomy and surrounding anatomy (70). The device may then be allowed to expand, or may be expanded, to cause hemostasis at the arteriotomy (72), and the closure assembly and introducer may be withdrawn away from and detached from the expanded device, leaving a closed arteriotomy (74).

Figure 6K:
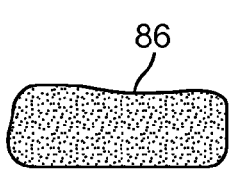
FIGS. 6A-6X illustrate various aspects of arteriotomy closure configurations wherein a collapsed closure device may be controllably rotated relative to an elongate deployment member to prevent withdrawal of the closure device through the arteriotomy.
Figure 6L:
Figure 6L:
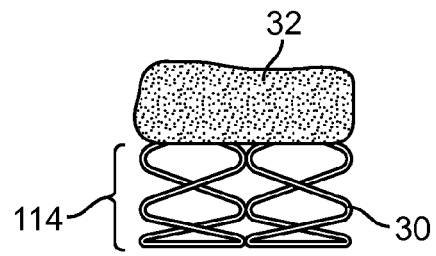
Figure 6M:
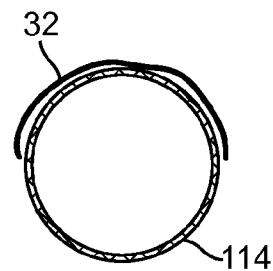
Figure 6O:
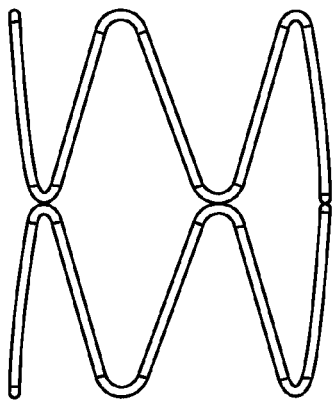
Figure 6P:
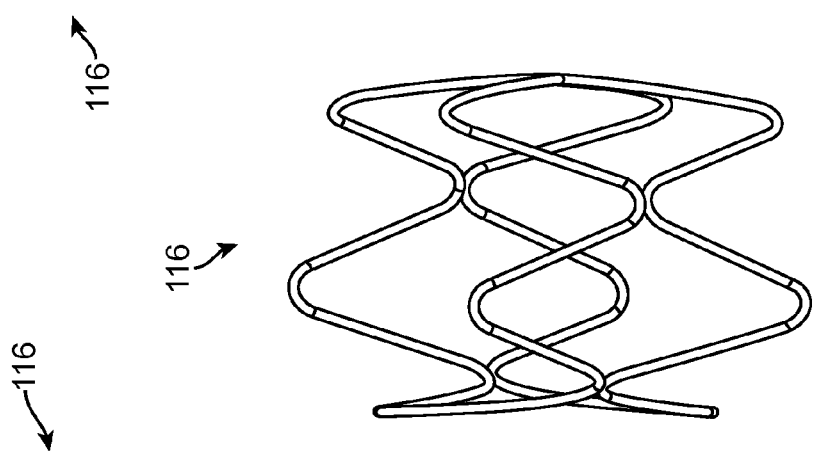
Figure 6N:
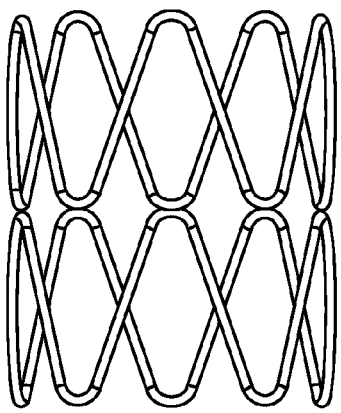
Figure 6R:
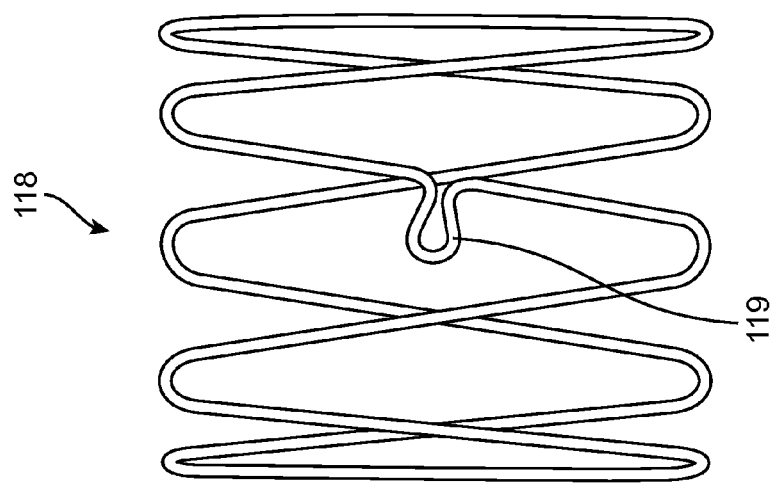
Figure 6Q:
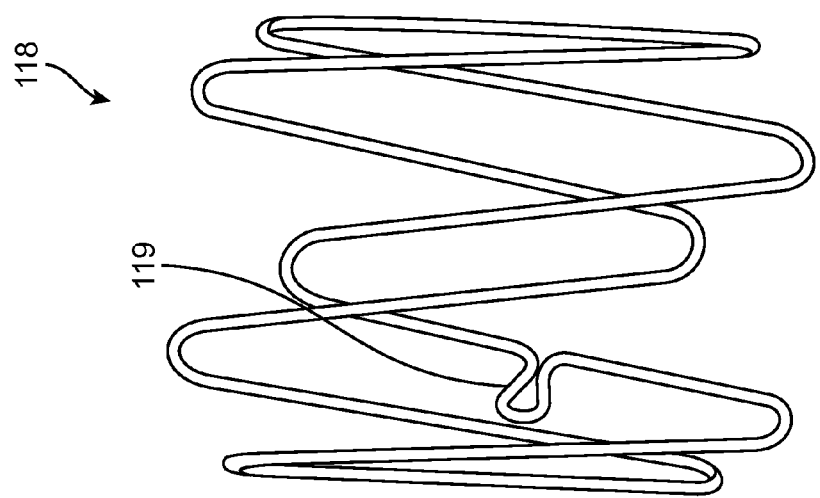
Figure 6S:
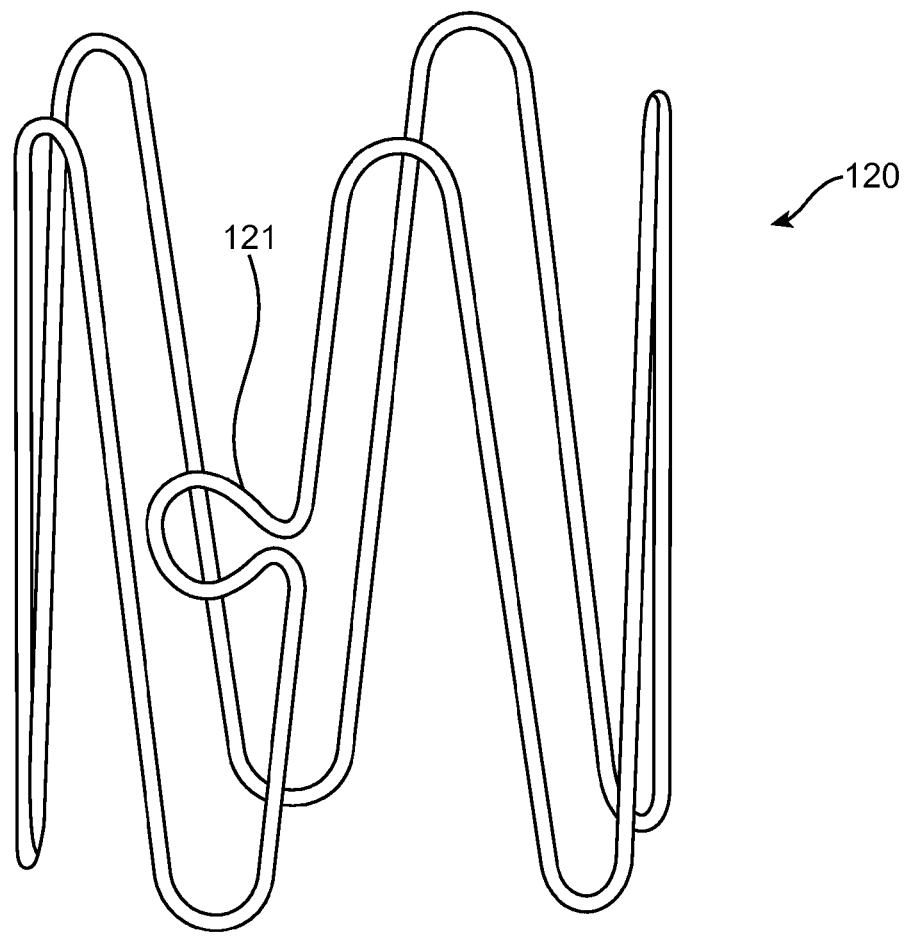
Figure 6U:
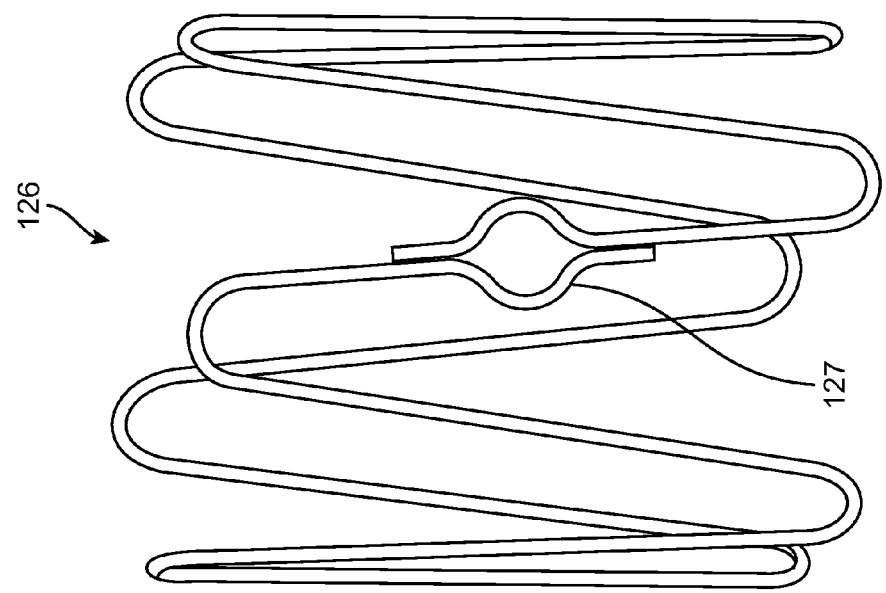
Figure 6T:
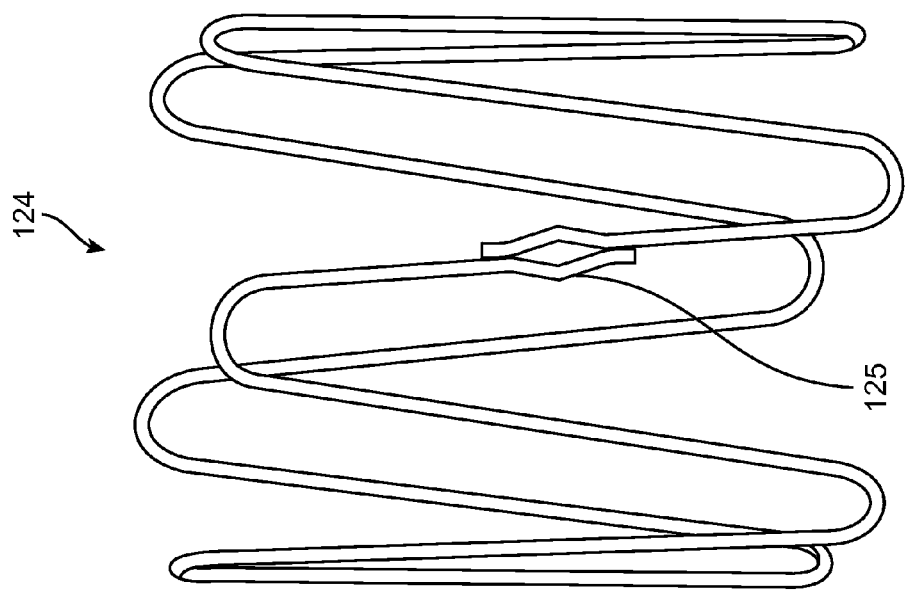
Figure 6V:
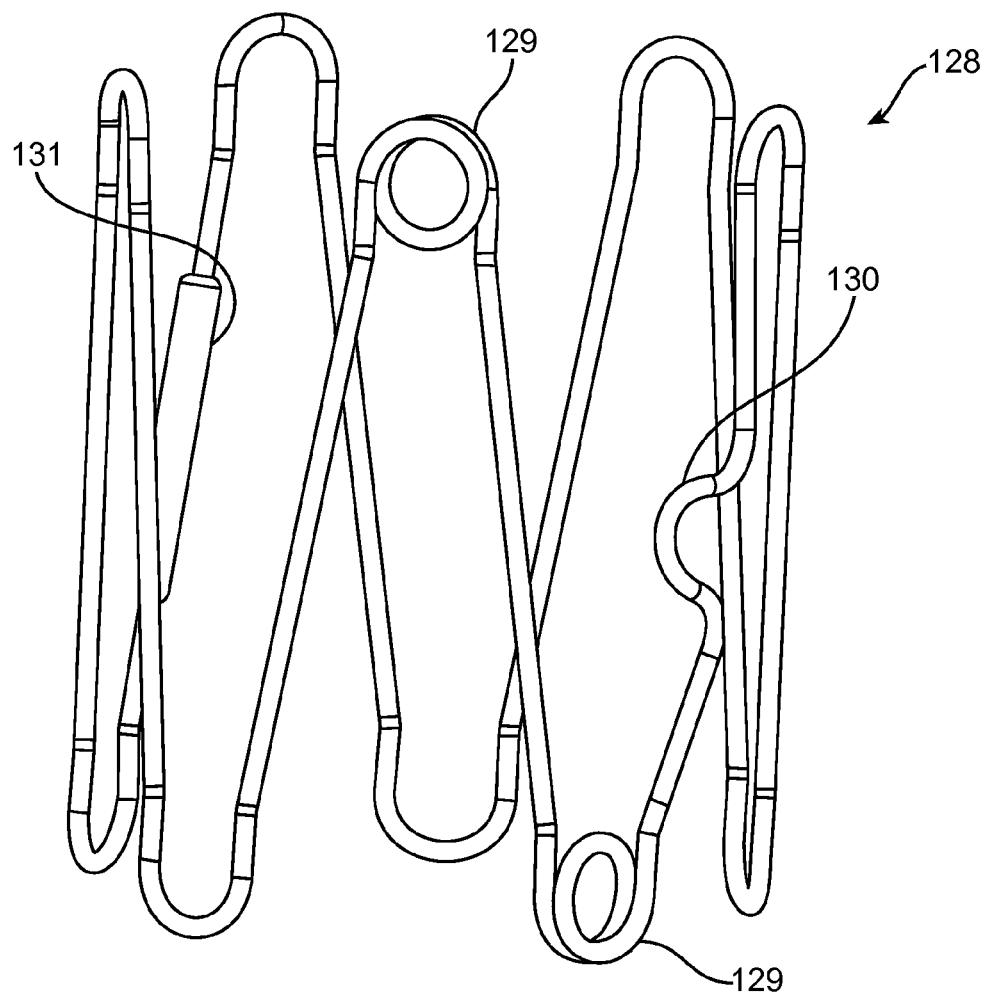
Figure 6W:
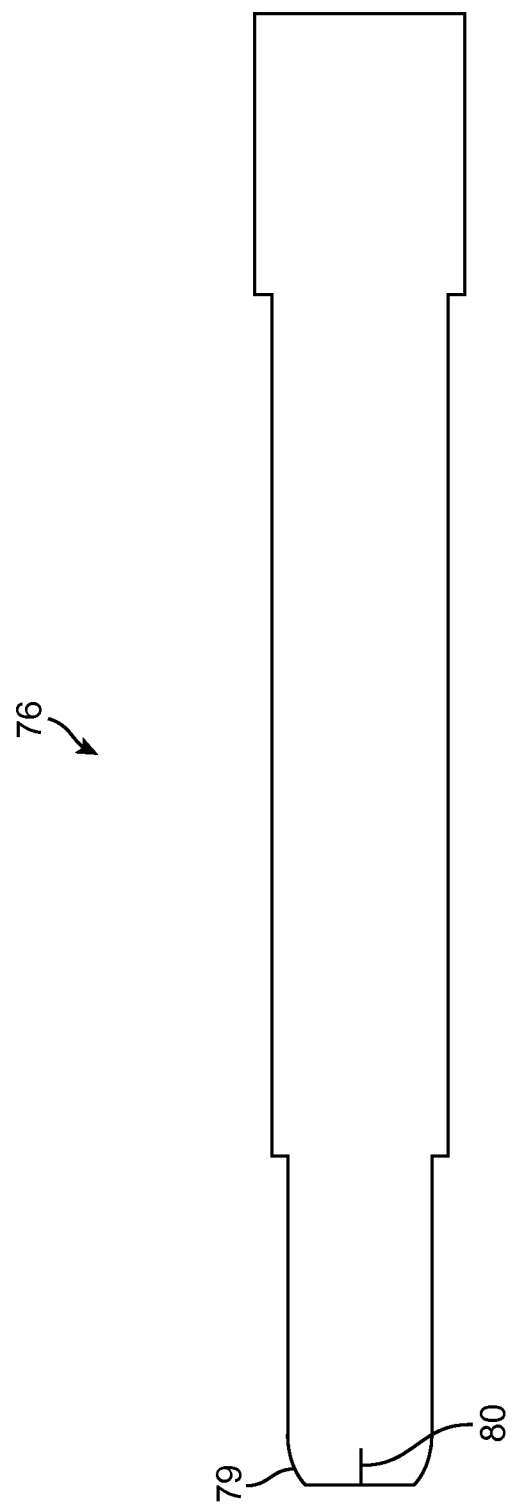
Figure 6X:
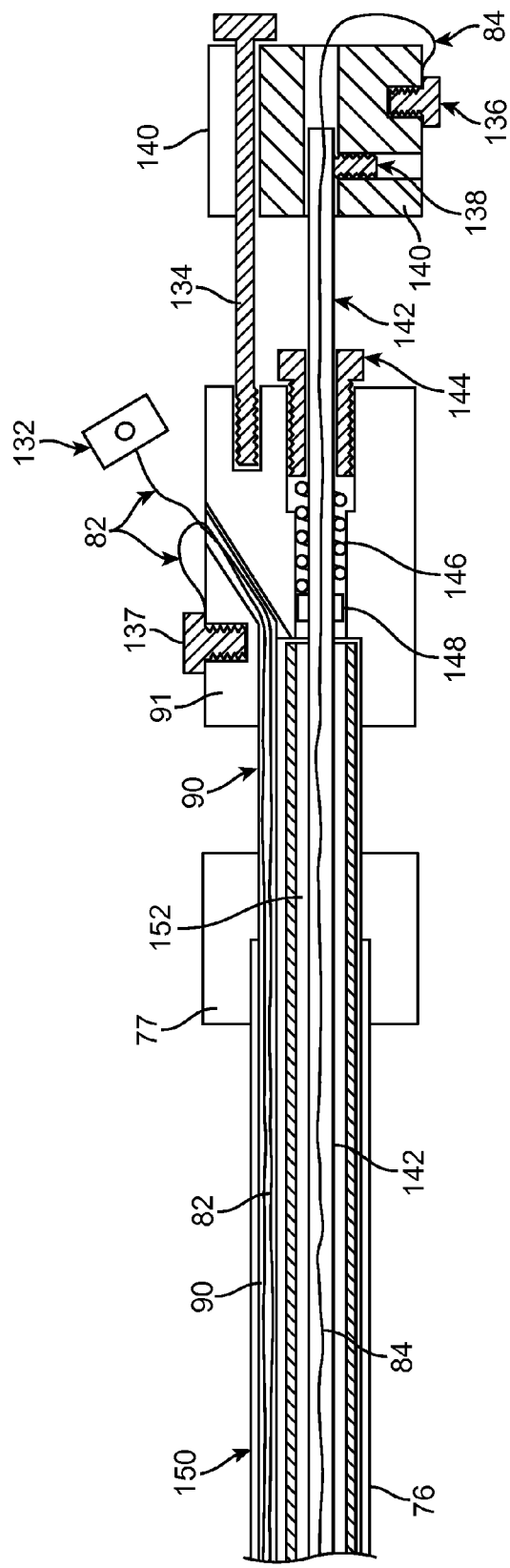

Referring to FIGS. 6A-6X, various aspects of another embodiment of a closure assembly are depicted, wherein a collapsed closure device may be controllably repositioned and/or reoriented during a deployment process in a manner that geometrically prevents such device from escaping the arteriotomy as other delivery tools subsequently are removed, and also limits or reduces blood or other fluids from escaping the arteriotomy once the device has been expanded into a final configuration, thereby effectively closing the arteriotomy. Referring to FIG. 6A, a delivery assembly is depicted comprising an outer introducer sheath (2), a delivery sheath (76) placed through the working lumen of the introducer sheath (2), and a arteriotomy closure device deployment assembly threaded through the working lumen of the delivery sheath (76), the assembly being depicted in FIG. 6B without the sheaths and featuring a collapsed closure device (86) coupled to both an elongate deployment member (90) and a foot member (92), the foot member being threaded through a working lumen defined by a portion of the deployment member (90). The closure device (86) may comprise an expandable frame, scaffold, or prosthesis with or without associated sheetlike members and/or cover members, and may be similar to those described above in reference to FIGS. 1A-3D, or below in reference to FIGS. 6K-6V. A deployment tension member (82), such as a suture or wire, is threaded through another working lumen defined by a portion of the deployment member (90) and looped around the collapsed closure device (86) as well as a portion of the foot member (92) to maintain the collapsed configuration of the closure device until the deployment tension member is tensioned, causing a releasable knot (83), such as a highwayman's hitch, to release and allow the collapsed closure device to expand or be expanded. An attachment tension member (84), such as a suture or wire that may be resorbable, akin to the attachment tension members (20, 21) described above, is threaded through a lumen or channel defined by the foot member (92) and tied to the closure device (84).

Referring to FIGS. 6C-6E, one configuration for controllably repositioning and/or reorienting a collapsed closure device (86) during deployment is configured. As shown in FIG. 6C, application of a load (100) to the elongate deployment member (90) initially will result in a compressive load at the interface (94) between the elongate deployment member (90) and the collapsed closure device (86). This compressive loading may result in translational repositioning of the closure device (86) initially until there is no more slack in the attachment tension member (84), after which a moment will be effectively applied to the closure device (86), causing it to rotate (98), or rotationally reorient, relative to the elongate deployment member, as depicted in FIGS. 6D and 6E. FIG. 6E, in particular, diagrammatically illustrates that a compressive interfacial load (94) applied along with a tensile load (96) through the attachment tension member (84) attached at a different location from the interfacial load application results in a rotation actuation. In one embodiment, rotational actuation may be accomplished by both actively tensioning the attachment tension member (84) and actively pushing the elongate delivery member (90). In other embodiments, only one of such members (84, 90) may be actively loaded, with the other kept relatively stationary. For example, referring to FIG. 6D, the attachment tension member (84) is shown grounded or anchored at a proximal location, so that rotation of the collapsed closure device (86) may be induced merely with compression or pushing upon the elongate deployment member (90) after slack in the attachment tension member (84) has been eliminated. Such rotation causes bending or hinging of a distal portion of the foot member at a predetermined hinge or bending axis (102), and the amount of rotational reorientation may be physically limited by the positions of distal portions of the elongate delivery member (90).

Referring to FIGS. 6F-6H, components of the above-described delivery assembly are shown disassembled to some degree. FIG. 6F depicts a foot member (92) coupled to a collapsed closure device (86) with a deployment tension member (82) and attachment tension member (84). FIG. 6G illustrates an elongate deployment member comprising a first guide tube (104) coupled to a second guide tube (106) with a deployment member outer layer (108), as shown in the orthogonal view of FIG. 6H. Both guide tubes (104, 106) define working lumens therethrough (150, 152, respectively). In the assembly of FIG. 6C, for example, a deployment tension member (82) may be passed through the first guide tube lumen (150), and a foot member (92), which itself defines a lumen through which an attachment tension member (84) may be passed, may be placed through the second guide tube lumen (152).

Referring to FIGS. 6I and 6J, orthogonal side views of a foot member (92) embodiment are depicted. In the depicted embodiment, the proximal portion (142) of the foot member may comprise a flexible tube comprising a polymer such as fluorinated ethylene-propylene, and the distal portion (110) may comprise a mechanically flattened continuation of such tubing configured with holes (112) to accommodate knots and fastening of a deployment tension member (element 82 in FIG. 6C, for example) and/or attachment tension member (element 84 in FIG. 6C, for example). A crease is provided to create a preferred bending or hinging axis (102) between the proximal (142) and distal (110) portions of the foot member. In another embodiment, the proximal portion (142) of the foot member may comprise a reinforcing material or member, such as a piece of metal hypotube, to increase the structural modulus of such portion and facilitate precise positioning and loading of such portion to maneuver the delivery assembly or portions thereof.

Referring to FIGS. 6K-6M, as described above, the closure device may be an expandable or self expanding device that is configured to be transformable from a collapsed state to an expanded state when unrestrained, in the case of a self expanding configuration, or unrestrained and actively expanded (for example, with an expansion balloon), in the case of an actively expandable configuration. Expansion of one embodiment is depicted in the transformation between FIG. 6K and FIG. 6L, wherein the collapsed closure device (86) is freed from the constraints of one or more restraining members, such as a lumen or lumens of one or more sheaths, or one or more deployment attachment members which may be looped around the collapsed configuration. FIG. 6M illustrates an orthogonal view of the expanded configuration of FIG. 6L. The expanded configuration of the depicted embodiment, illustrated in FIGS. 6L and 6M, comprises an expanded form of an expandable closure device (114) featuring a cylindrical pattern of nitinol frame elements or structural members (30), coupled to a cover structure (32), similar to those described above in reference to FIGS. 1A-1J and 2A-2I. A sheetlike member may also be coupled to the frame elements to assist with arteriotomy closure, as described above. As described above, preferably the cover (32) is sized to not only contain substantially the entire structure when in a collapsed configuration, but also to provide an additional layer of arteriotomy closure and leak prevention when the device has been expanded and the cover (32) has been oriented directly adjacent the location of the arteriotomy. Also as described above, the cover (32) may comprise a bioresorbable material, and in other embodiments, elements of the closure device (14, 24) structure may comprise a polymeric material which also may be bioresorbable. The cover (32) may be coupled to the closure device (114) using a clip, wire, or suture which may be looped around one of the frame elements (30) and through the material comprising the cover (32). Geometric features may be created in the closure device to assist with such coupling, and may be configured to allow for coupling of the cover and closure device without a clip, wire, or suture.

Referring to FIGS. 6N-6O, three different views of a closure device frame or scaffold (116) configuration comprising two crowns coupled together, using a weld or adhesive junction, for example, are illustrated. A clip, wire, or suture around one of the crown junctions may be utilized to couple a cover to such device.

Referring to FIGS. 6Q and 6R, two different views of a closure device frame or scaffold embodiment (118) are shown wherein a small loop feature (119) has been formed to assist with the coupling of such scaffold and a cover. FIG. 6S depicts a similar embodiment (120) having a larger loop feature (121). FIG. 6T depicts an embodiment (124) wherein a loop feature (125) is formed with an end to end structural member junction that may comprise welds or adhesive junctions; FIG. 6U depicts a similar embodiment (126) with a larger loop feature (127). FIG. 6V depicts an embodiment (128) having several features of interest, including an end to end crimp tube junction (131), a small bend feature (130) which may be positioned to contain or assist with coupling an associated cover member, and two pinch coil features (129) configured to retain a portion of a cover member with a pinch friction/load fit, somewhat akin to that provided to a piece of paper with a paper clip. In other embodiments, pinch coil features (129) may be created at various locations about the closure device frame or scaffold structure, in addition to the end apex locations as shown in the variation of FIG. 6V.

FIG. 6W illustrates a side view of a delivery sheath (76), which may comprise a generally cylindrical polymeric tube with sequentially stepped down outer diameter shaping (to provide greater flexural modulus performance and shaping distally) and an atraumatic tip (79) similar to that shown in FIG. 6A (element 78 of FIG. 6A) comprising a partially hemispheric or capsular arcuate geometry with notches (80) to allow for passage of closely fit objects (i.e., by bending forward/distally one or more of the plurality of atraumatic tip flaps formed by the notches 80 and capsular shape of the atraumatic tip 79) through a working lumen which preferably is formed and defined through the sheath (76). As described above, the introducer illustrated in FIG. 6A, for example, has similar atraumatic tip features, including a notched (80) partially hemispheric or capsular arcuate geometry (element 78 of FIG. 6A) configured to accommodate the passage of relatively closely fit objects (i.e., by bending forward/distally one or more of the plurality of atraumatic tip flaps formed by the notches 80 and capsular shape of the atraumatic tip, element 78 of FIG. 6A).

FIG. 6X illustrates aspects of the proximal portions of a delivery assembly which may be utilized with a distal deployment configuration such as that illustrated in FIG. 6A. Referring to FIG. 6X, the outermost layer of the distal aspects of the depicted configuration comprises the delivery sheath (76), which terminates proximally with a delivery sheath hub (77) configured to be manipulated by an operator. Within the lumen defined by the delivery sheath is a delivery assembly comprising an elongate deployment member (90) movably coupled to a foot member proximal portion (142). The elongate deployment member (90) terminates proximally with an elongate deployment member hub (91) configured to be manually manipulated by an operator. This hub (91) features a releasable termination screw to fix one end or one portion of a deployment tension member (82), the other portion or end of which may be coupled to a pull tab (132) configured for tension manipulation by an operator—to, for example, untie a highwayman's hitch knot configured to releasably contain a closure device in a collapsed configuration. The elongate deployment member hub (91) also features a screw (144) adjustable compression spring (146). The proximal portion of the foot member (142) terminates proximally in a foot hub (140) configured to be manually manipulated by an operator. A set screw (138) may be utilized to fasten the hub (140) to the. The attachment tension member (84) is proximally routed through the proximal portion of the foot member (142) to a releasable fixation screw (136) proximal portion of the foot member (142), which, as described above, may be reinforced by, or may comprise, a relatively stuff material or construct, such as a metal hypotube. In operation, when an operator wants to induce rotation and/or translation of a collapsed closure device, as described, for example, in reference to FIGS. 6C-6E, he may longitudinally reposition the elongate deployment member hub (91), foot member hub (140), and attachment tension member (84) tensioning to create such rotation and/or translation of the distal foot portion and collapsed closure device. A compression spring seat (148) coupled to the proximal portion of the foot member (142) applies loads to the proximal portion of the foot member (142) as the foot member hub (140) is pushed toward the elongate deployment member hub (91). A shoulder bolt (134) maintains the orientation of the foot member rotationally to allow the operator to understand the direction of flexion of the foot member upon desired rotation and/or translation. The compression spring adjustment screw may be tightened to pre-bias the distal foot portion to flex when released from constraining members, such as one or more sheaths which may temporarily surround and mechanically constrain the distal foot portion (i.e., thereby urging the distal foot straight as opposed to flexed). Alternatively, the spring may be left relatively unloaded to allow for release from constraining members without pre-biased flexion actuation, followed by controlled flexion actuation using the various hubs and attachment tension element. Aspects of embodiments of such operation are described in reference to FIGS. 7A-7F, and 8A-8B.

Figure 7A:
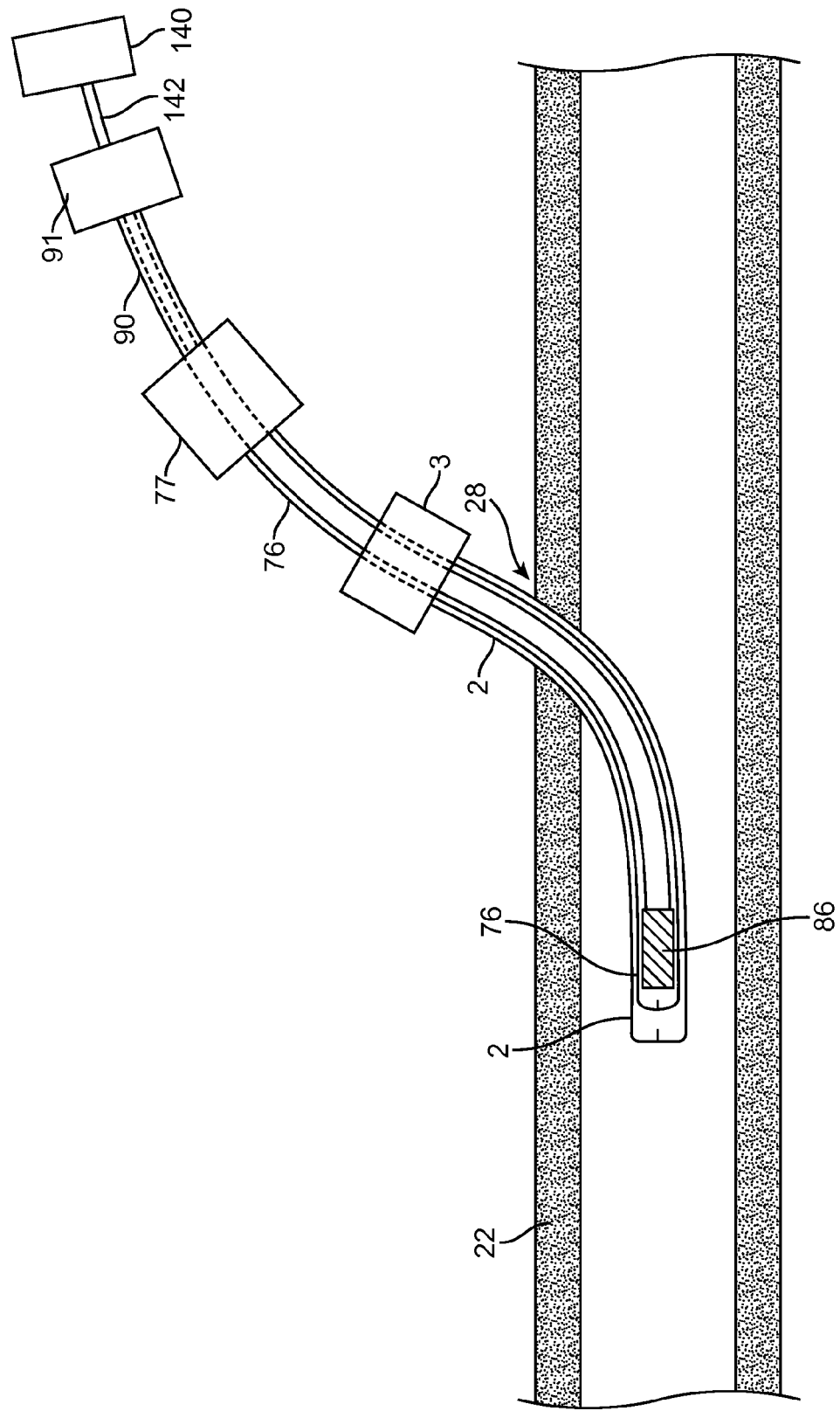
FIGS. 7A-7F illustrate various aspects of an arteriotomy closure device deployment wherein a collapsed closure device may be controllably rotated relative to an elongate deployment member to prevent withdrawal of the closure device through the arteriotomy.
Figure 7B:
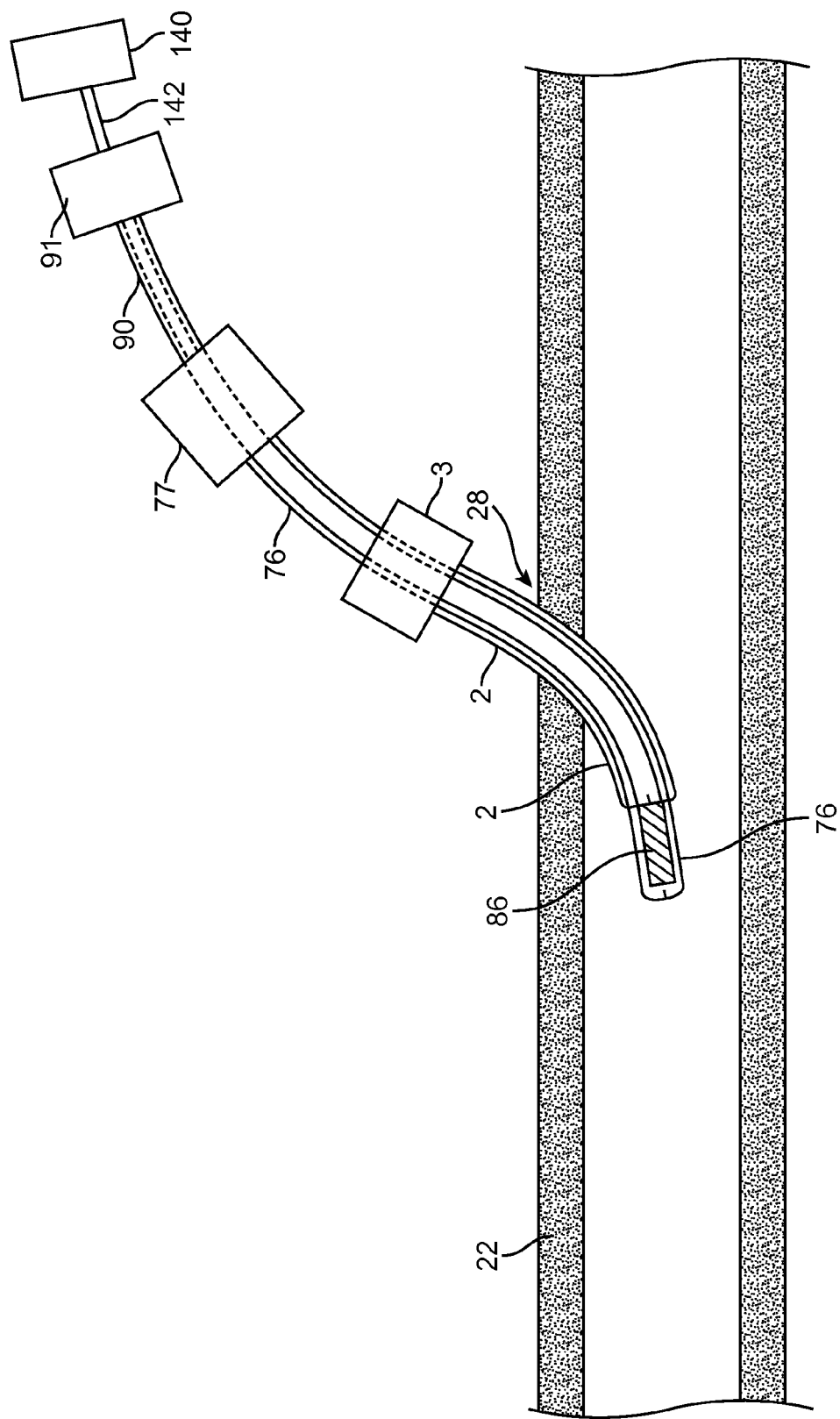
Figure 7C:
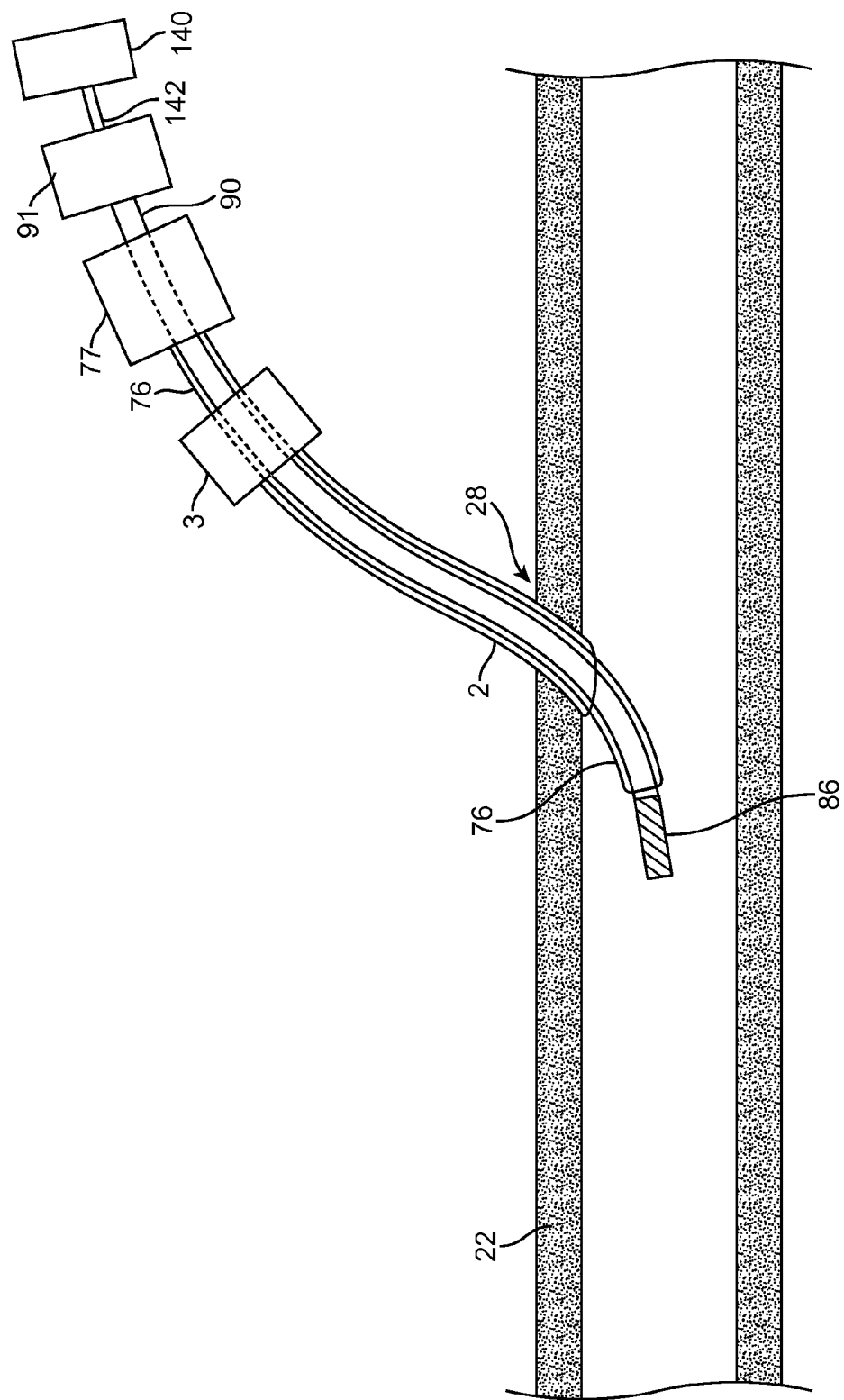
Figure 7D:
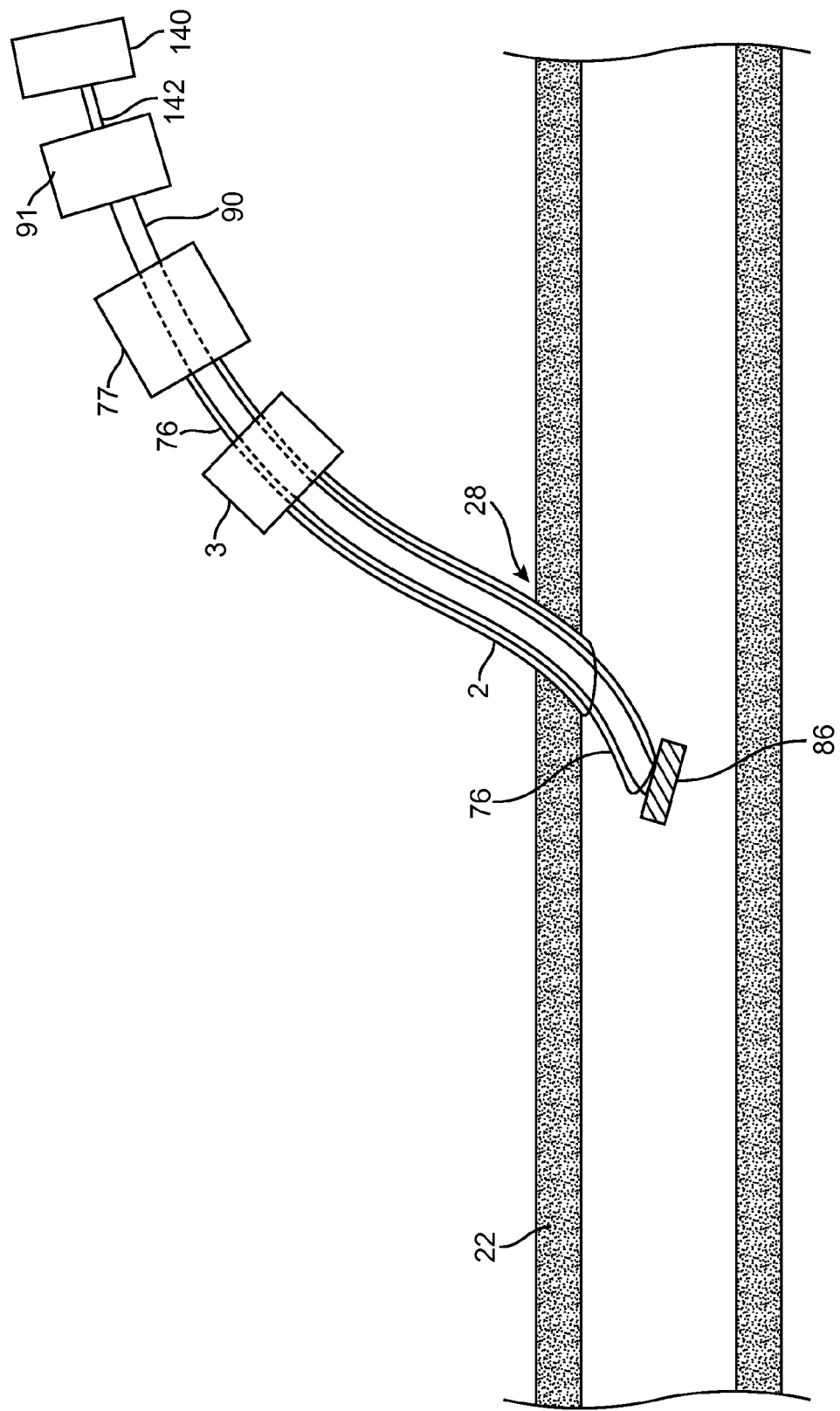
Figure 7E:
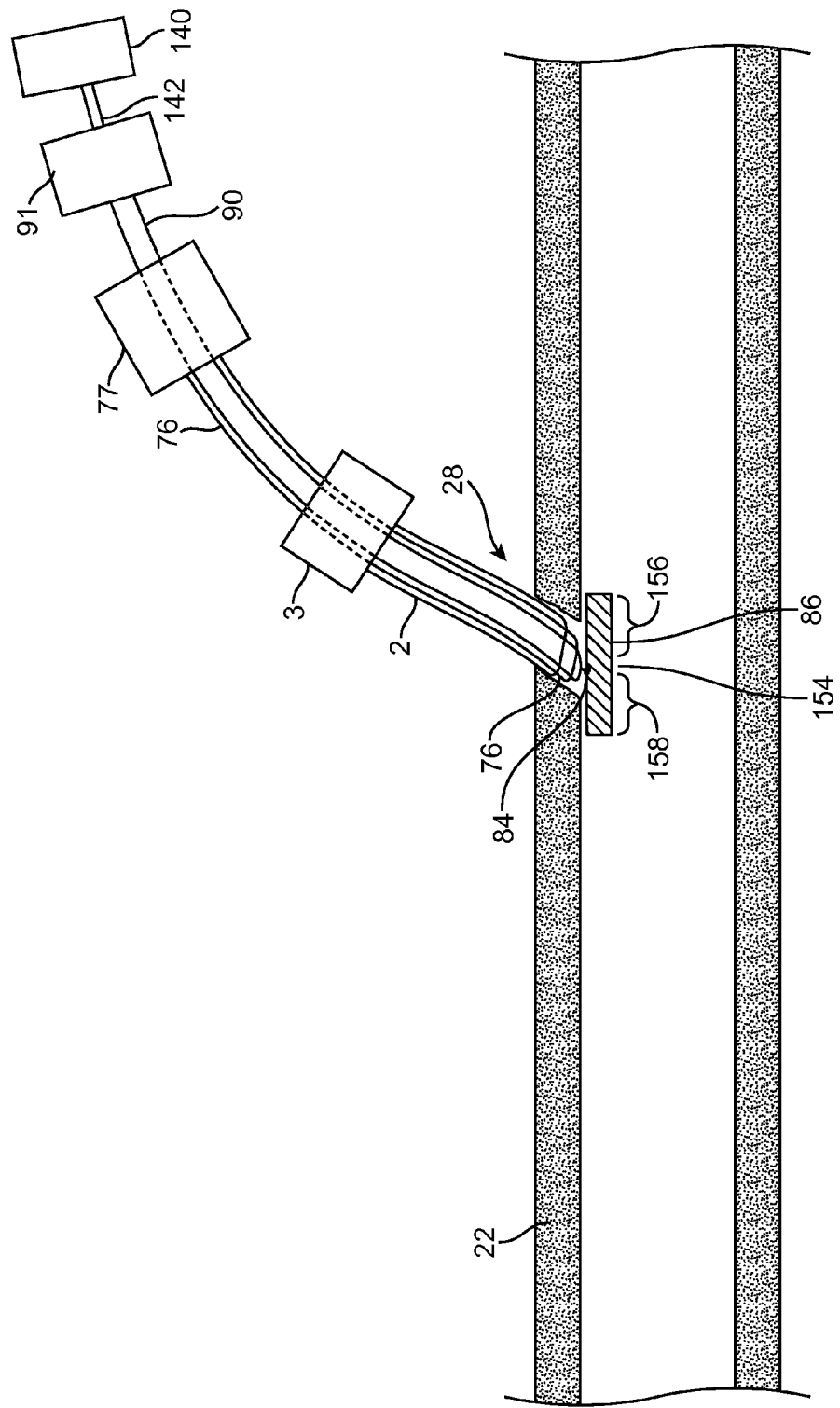
Figure 7F:
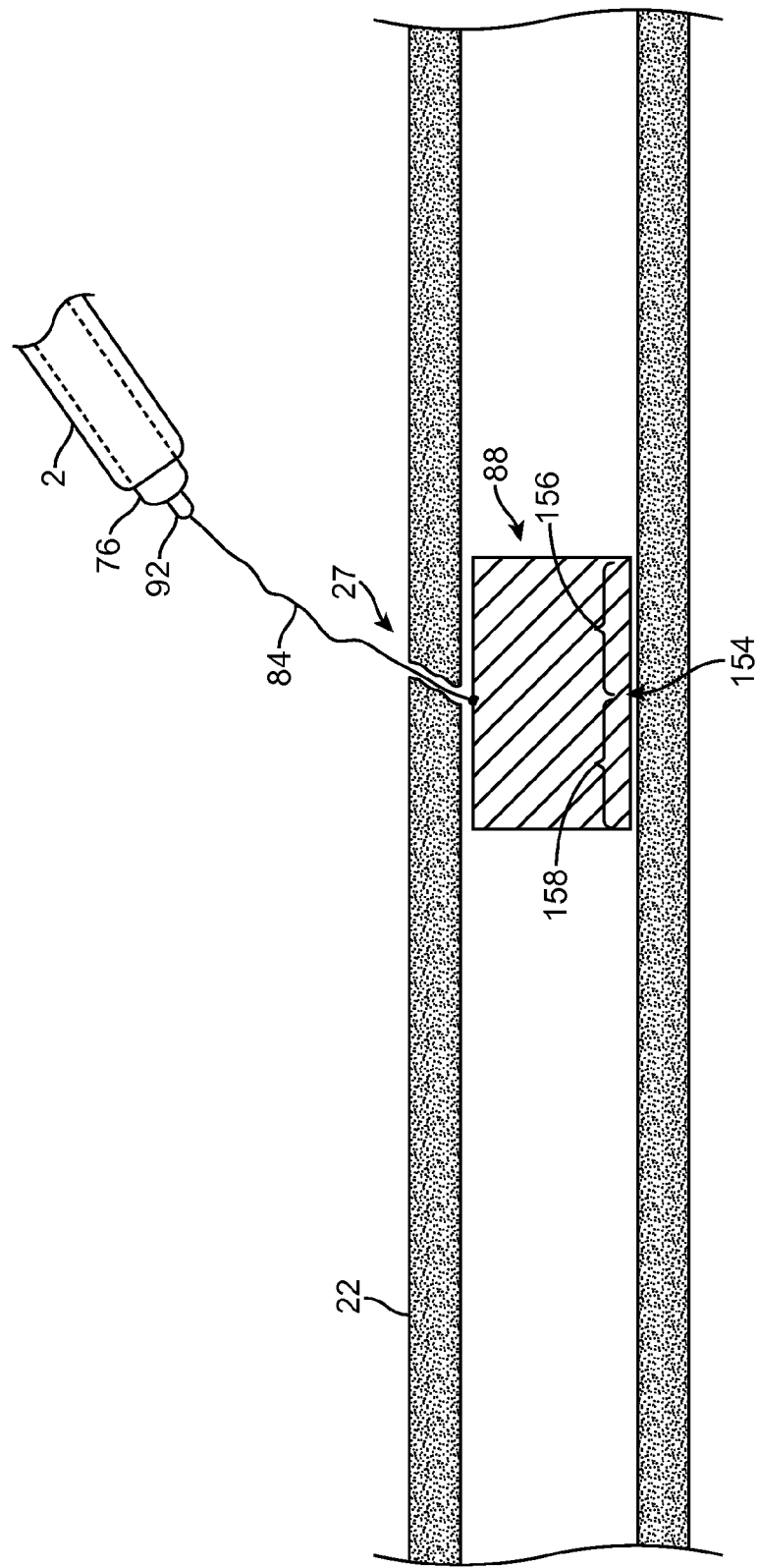

Referring to FIG. 7A, an assembly has been inserted through an arteriotomy (28) and advanced forward to place a collapsed closure device (86), such as those described above in reference to FIG. 1A-1J, 2A-2I, 3A-3D, or 6L-6V, within a blood vessel (22) and surrounded by one or more sheaths (76, 2). In some embodiments, the arteriotomy (28) may have a diameter as large as 18 French or greater. Referring to FIG. 7B, to begin deployment of the closure device (86), the introducer sheath (2) may be withdrawn proximally using an introducer manipulation hub (3), and/or the elongate deployment member (90) and foot member (142) may be advanced distally, to further expose the collapsed closure device (86). Referring to FIG. 7C, the delivery sheath (76) and collapsed closure device (86) may be moved relative to each other to further expose the collapsed closure device (86). Referring to FIG. 7D, the exposed collapsed closure device (86) may be controllably translated and/or rotated to cause rotational reorientation to a toggled position. Referring to FIG. 7E, the closure device (86) is intentionally dimensioned to not be easily passable through the arteriotomy when in the toggled position. In one embodiment, the closure device (86) may have a proximal portion, centerpoint, and distal portion along an axis parallel to a longitudinal axis of the closure device when collapsed or expanded. Preferably the total length of the device along this axis is greater than the largest dimension of the arteriotomy, and preferably the distal portion and proximal portion are long enough to prevent additional rotation of the device relative to the vessel. In one embodiment, the attachment tension member (84) may be tensioned to place the collapsed closure device (86) against the arteriotomy with the central point (154), adjacent to which the attachment tension member preferably is terminated upon the device, aligned with the center of the arteriotomy (28), and the proximal (156) and distal (158) portions of the device extending away from the arteriotomy (28). In other words, upon controlled repositioning and/or reorientation of the collapsed closure device to the toggled or rotated position, further withdrawal of the closure device out of the arteriotomy is prevented by virtue of the geometry of the arteriotomy and closure device, the device in the depicted embodiment (86 collapsed; 88 expanded) spanning across the diameter of the previous arteriotomy location with extra length to spare on either side of this previous arteriotomy location. Referring to FIG. 7F, the deployment tension member (not shown) has been tensioned to allow the closure device to take its expanded shape (88), preferably urging the associated cover against the inside of the arteriotomy, which shrinks to a closed configuration (27) when all of the hardware has been withdrawn with the exception of the attachment tension member (84), which is configured to remain attached to the expanded device (88), and is preferably configured to subsequently biologically erode after being clipped most proximally and allowed to stay inside of the body after transcutaneous wound closure.

Figure 8A:
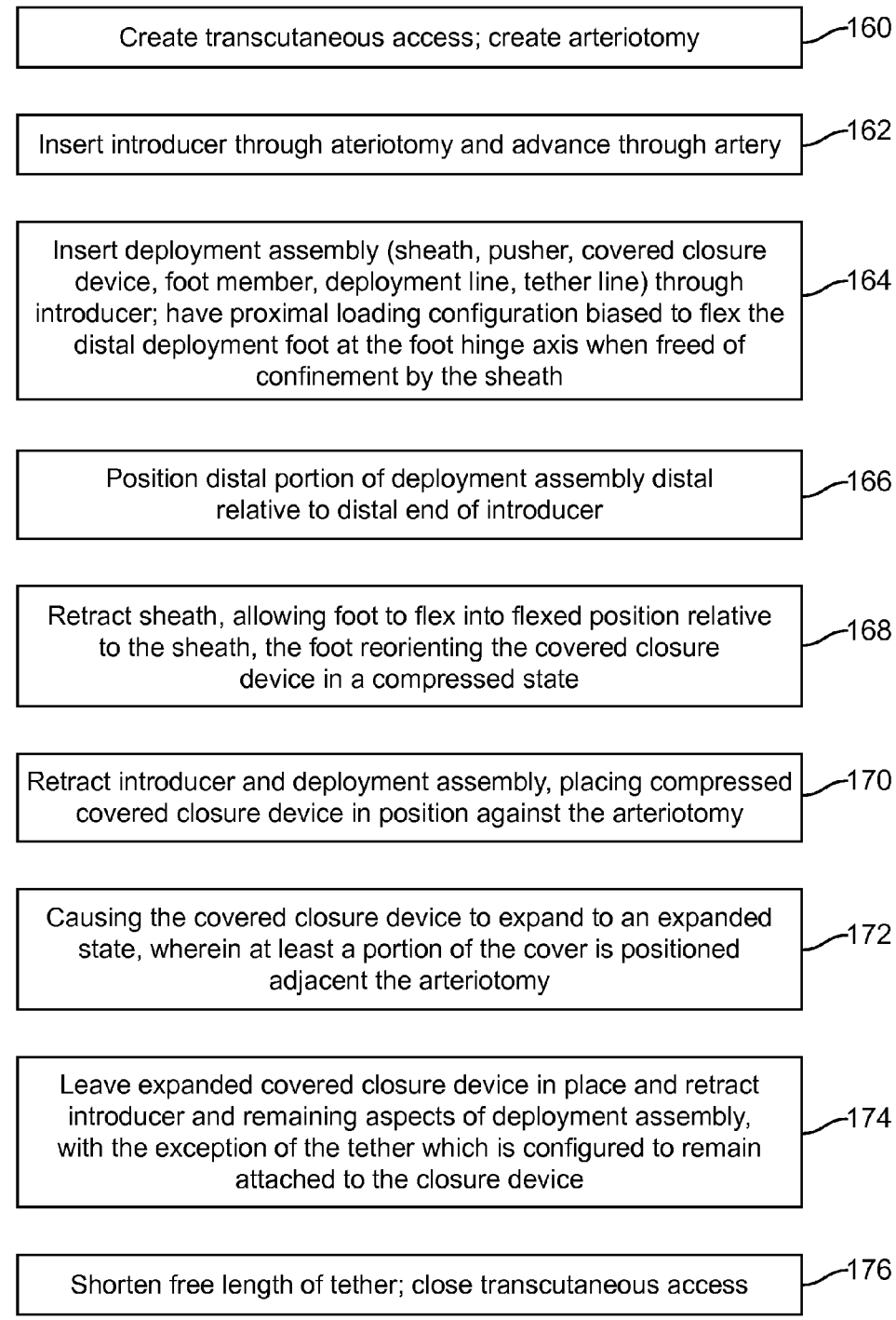
FIG. 8A illustrates aspects of deployment steps using a configuration such as that illustrated in FIGS. 6A-6X, wherein a foot is pre-biased to flex once released from a restraining sheath.

Referring to FIG. 8A, a deployment process is outlined, wherein subsequent to transcutaneous access and arteriotomy creation (160), an introducer and associated hardware may be inserted through the arteriotomy and advanced through a portion of the artery (162). A deployment assembly may be advanced (164) with the introducer, or subsequently advanced, and may be exposed by moving the introducer longitudinally relative to the deployment assembly. In one embodiment wherein the foot member is pre-biased to reorient by a proximal loading configuration such as a compressed compression spring, when the distal portion of the foot member is cleared of mechanical confinement by a delivery sheath or introducer sheath, it flexes at the foot hinge or bend axis to reorient the collapsed closure device. In preparation for such reorientation, the introducer may be moved proximally relative to the closure device (166). In the depicted embodiment wherein the foot member is pre-biased to flex when not constrained, the last anti-flexion constraint, the delivery sheath, is withdrawn relative to the foot member, closure device, and elongate delivery member, and the closure device and distal portion of the foot become reoriented (168). Subsequently, the introducer, delivery sheath, and foot member/elongate delivery member assembly may be withdrawn to allow the closure device to be urged against the arteriotomy with tension in the attachment tensile member (170). Subsequently, the deployment tension member may be controllably tensioned to allow the closure device to expand in position against the arteriotomy, preferably with a cover portion of the closure device positioned immediately adjacent the arteriotomy location (172). The deployment and access tools may be withdrawn, leaving behind only the expanded closure device and the attachment tension member, or "tether line" (176), which may subsequently be shortened prior to transcutaneous access closure (176).

Figure 8B:
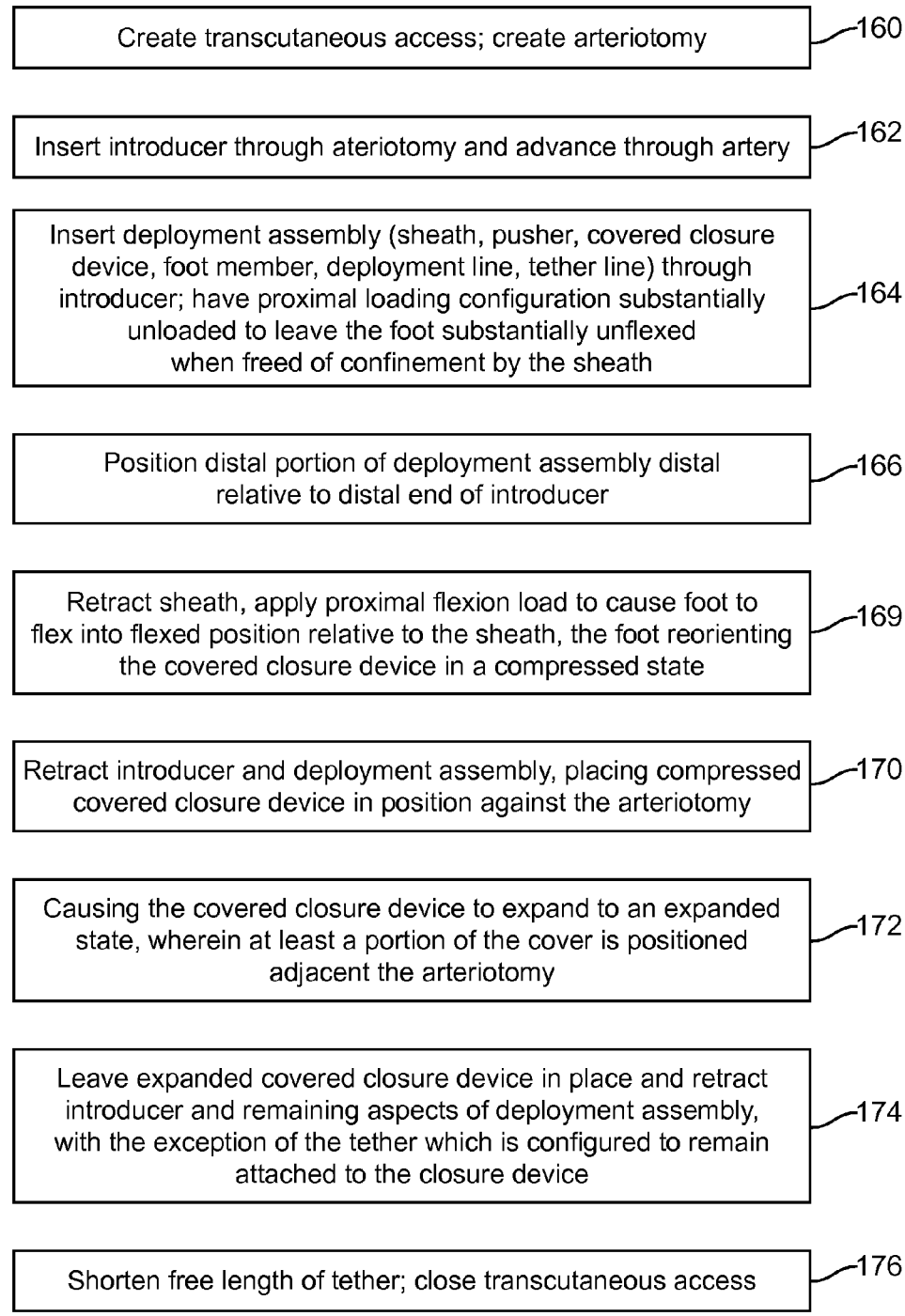
FIG. 8B illustrates aspects of deployment steps using a configuration such as that illustrated in FIGS. 6A-6X, wherein a foot is flexed after release from a restraining sheath, subsequent to application of a flexing load.

Referring to FIG. 8B, another embodiment is depicted, differing from that of FIG. 8A in that the foot member is not pre-biased to flex upon release from constraining members such as an introducer sheath or delivery sheath. In the embodiment of FIG. 8B, the collapsed closure device may be exposed to the bloodstream while the foot remains in an un-flexed configuration, and when the operator desires, may be controllably rotated and/or translated into the rotated configuration with a flexion inducing load applied deliberately (169).

Figure 9C:
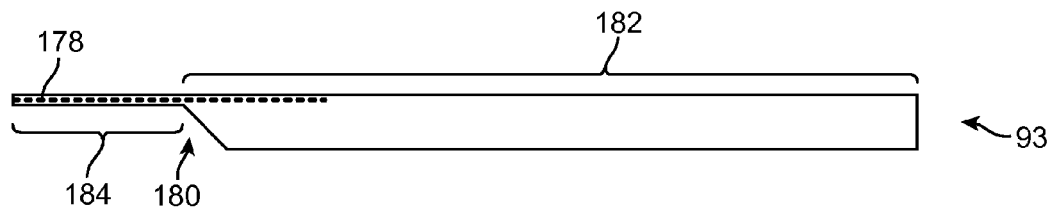
Figure 9D:
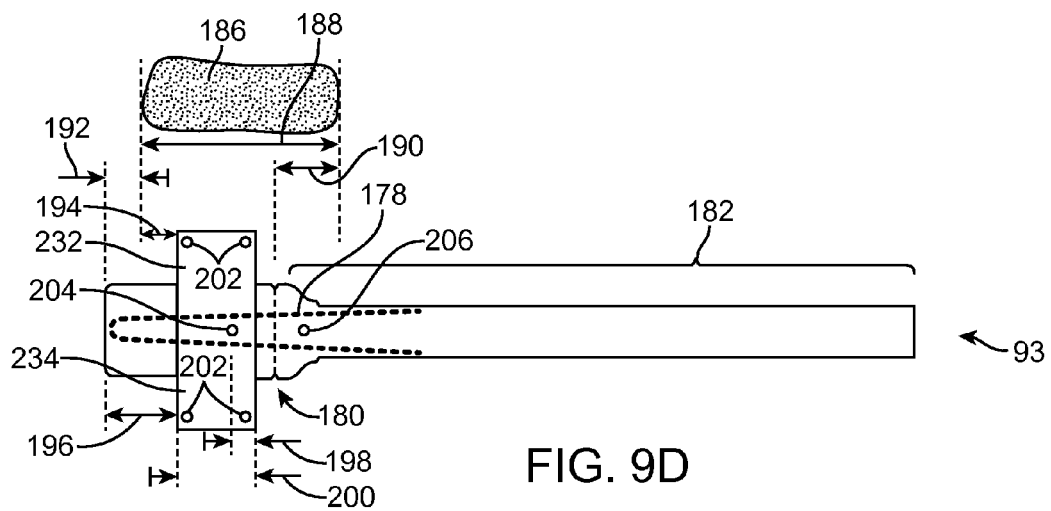
Figure 9E:
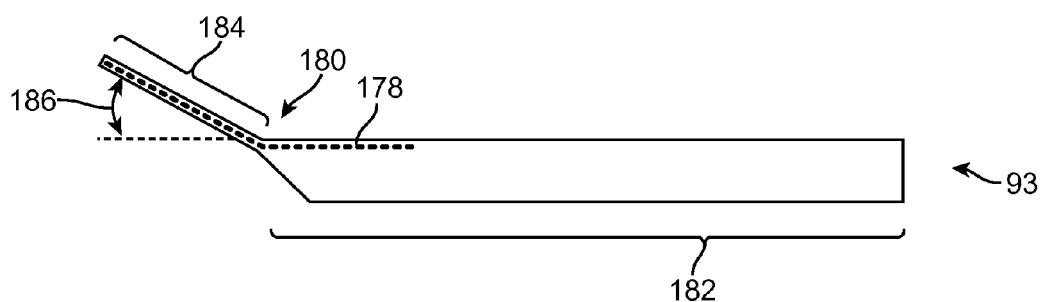

Referring to FIGS. 9A-9E, another closure device deployment embodiment is depicted, wherein an elongate bending spring member is built into the foot member to pre-bias the foot to flex when not constrained by a constraining structure such as a delivery or introducer sheath. Referring to FIG. 9A, an assembly somewhat similar to that depicted in FIG. 6A is depicted, with the exception that the foot member (93) comprises an elongate bending spring member (178) extending through the distal portion of the foot member, and also through some of the distal end of the proximal portion of the foot member. Preferably the elongate bending spring member (178) comprises a pre-bent metallic or polymeric member and is configured to assume a foot flexion position, as depicted in FIG. 9B, for example, when not otherwise constrained by a sheath or other contraining member to assume a straight position, as shown in FIG. 9A. In one embodiment the elongate spring member comprises nitinol superalloy wire in a "V" shape as in FIG. 9D, and is coupled to proximal and distal foot member structures using interference fitting and a discrete adhesive coupling at the distal tip of the "V" shape. In other embodiments, the elongate spring member may comprise other biocompatible metals, such as stainless steel, cobalt chrome, titanium, nickel, gold, tantalum and/or alloys thereof, as well as biocompatible polymeric materials such as polytetrafluoroethylene, expanded polytetrafluoroethylene, polyethylene terepthalate, polyesther, polylactic acid, poly glycolic acid, poly-lactic-co-glycolic acid, fluorinated ethylene-propylene, silicone, polyethylene, polyurethane, and/or copolymers of any of the above. Further details of an elongate spring foot member are depicted in FIGS. 9C-9E. Referring to FIG. 9C, the elongate bending spring member (178) extends nearly the entire length of the distal portion (184) of the foot member (93), and a relative small length of the distal end of the proximal portion (182) of the foot member (93). When allowed to rotate (i.e., without a sheath or other constraint holding it straight), as in FIG. 9E, the foot member distal portion (184) is configured to rotate to a preselected angle (186) in accordance with the pre-shaped configuration of the elongate spring member, about an axis of rotation, or bending or hinge point, (180) that divides the proximal portion (182) from the distal portion (184). Referring to FIG. 9D, an orthogonal view illustrates the placement of a collapsed closure device (86) relative to the distal portion (184) of the foot member, such distal portion (184) being in an unfolded configuration in FIG. 9D, to accommodate interfacing and coupling with a collapsed closure device (86). Four holes in the distal portion (184) of the foot are configured to assist with releasable fastening of a deployment tension member (element 82 in FIG. 9A) using a releasable knot, such as a high-wayman's hitch. The distal portion (184) of the foot member may be created by crushing flat a substantially cylindrical piece of tubing comprising the proximal portion (182) of the foot member, and creating an "H"-shaped slice in such flattened portion to create the wings (232, 234) configuration depicted in FIG. 9D. Each of the wings (232, 234) is configured to be wrapped around the exterior of a collapsed closure device (86) to form a stable saddle-like interface. Two additional holes (204, 206) are formed through the foot member (93), one (204) to accommodate a deployment tension member (element 82 in FIG. 9A), and the other (206) to accommodate an attachment tension member (element 84 in FIG. 9A). Some sample dimensions for one particular embodiment include a collapsed closure device length dimension (188) of about 0.5", a bending axis to proximal end of collapsed closure device dimension (190) of about 0.125", a distal tip of foot member to distal end of collapsed closure device dimension (192) of about 0.25", a distal end of collapsed closure device to distal wing edge dimension (194) of about 1/16", a distal end of foot member to distal wing edge dimension (196) of about 5/16", a deployment member hole to proximal wing edge dimension (198) of about 1/16", and a wing length dimension (200) of about 0.25".

Figure 10:
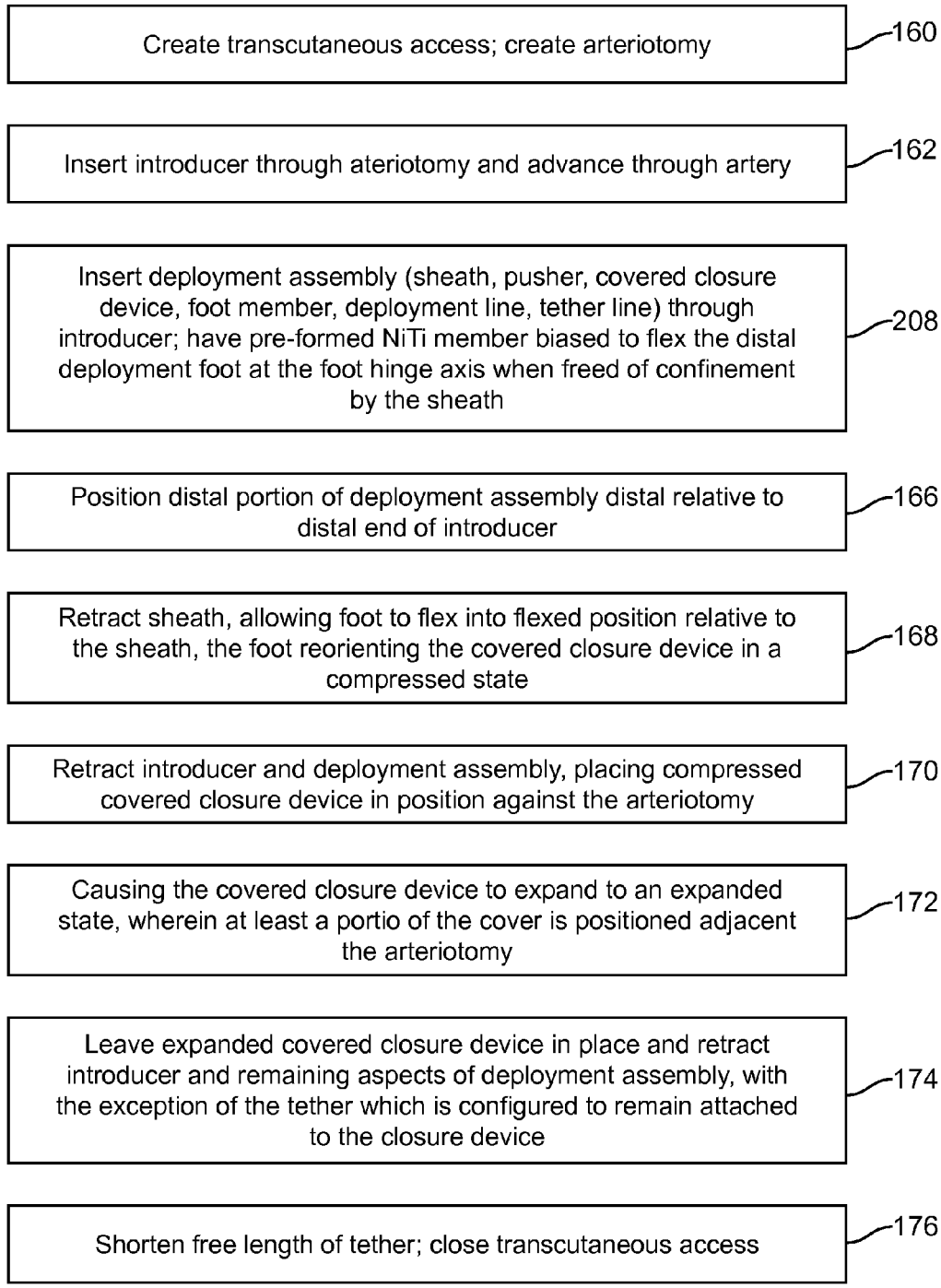
FIG. 10 illustrates aspects of deployment steps using a configuration such as that illustrated in FIGS. 9A-9E, wherein a foot is pre-biased to flex once released from a restraining sheath.

Referring to FIG. 10, a process for utilizing an arteriotomy closure system such as that described in reference to FIGS. 9A-9E is depicted, with steps similar to those described in reference to FIG. 8A, with the exception of inserting a deployment assembly wherein the associated foot member comprises a pre-formed nitinol ("NiTi" or nickel titanium alloy) member biased to flex the distal foot portion at the rotational (or hinge or bending) axis when freed of confinement by a confining structure such as a delivery or introducer sheath (208).

Figure 11:
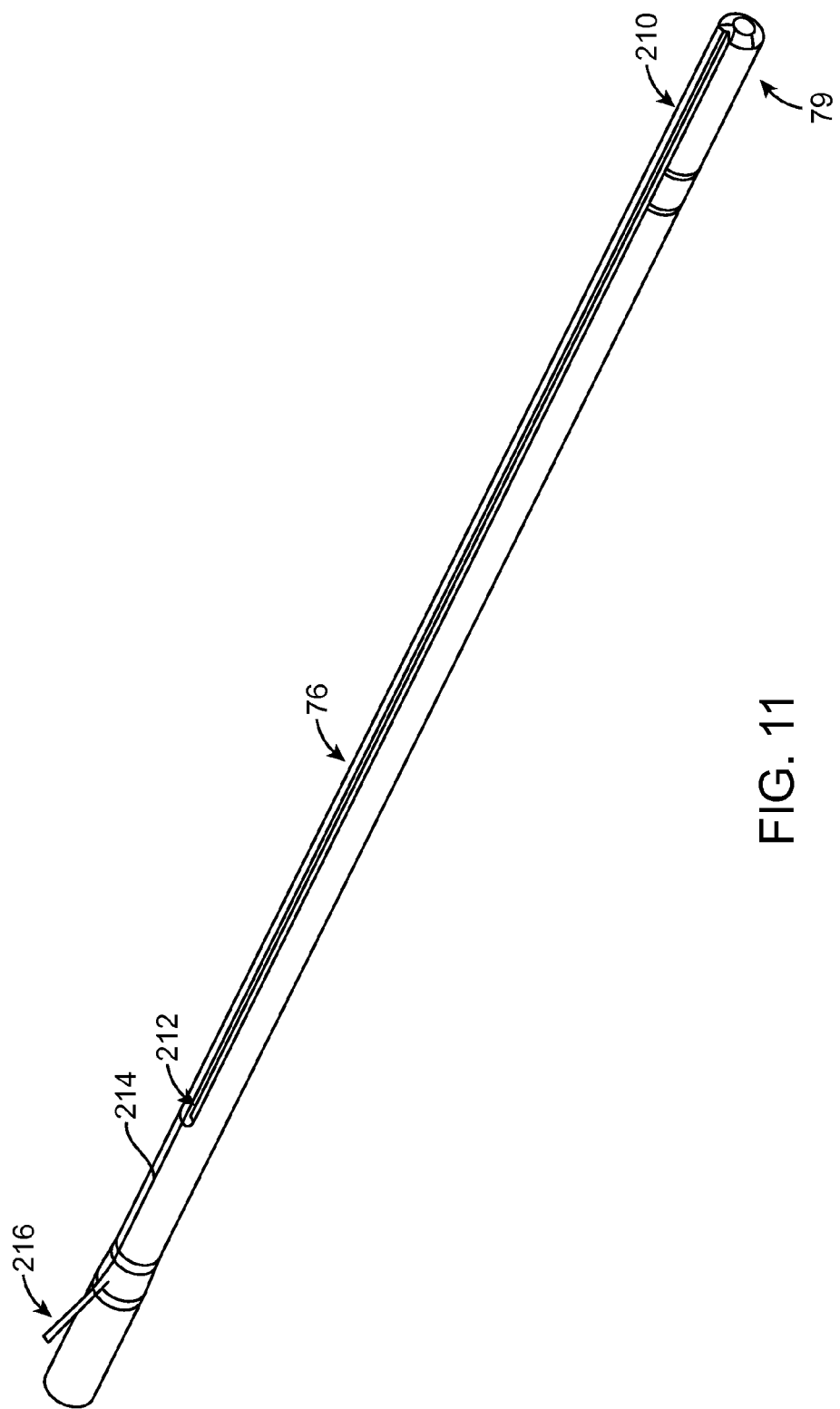
FIG. 11 illustrates aspects of a deployment sheath configured to assist an operator with positioning of related instrumentation adjacent an arteriotomy location.

Referring to FIG. 11, a particular embodiment of a deployment sheath (76) is depicted, wherein a blood channel (210) is formed within the exterior surface of the sheath (76) to allow pressurized blood, when present at the distal tip of the sheath (76), to flow from the distal end of the sheath, proximally through the channel (with an introducer sheath in place over the deployment sheath, the channel would be confined at the outer surface by the inside surface of the introducer lumen, but would remain free to flow through the channel proximally), to a lumen inlet (212), the associated lumen (214) being fluidly connected with a simple indicator fitting (216) configured to effectively ooze or squirt blood when appropriate blood pressure is present at the distal end of the channel (210). Such a configuration may be utilized in the relatively high-pressure (relative to venous) arterial system where arteriotomies are created, to provide an indication to an operator that the distal portion of the subject sheath (79) is exposed to arterial flow. In one embodiment, such an indication may be utilized to position the distal portion of such sheath (79) just at the transition out of the arteriotomy and into non-pressurized space, when conducting a closure device deployment, as described above.

Figure 12A:
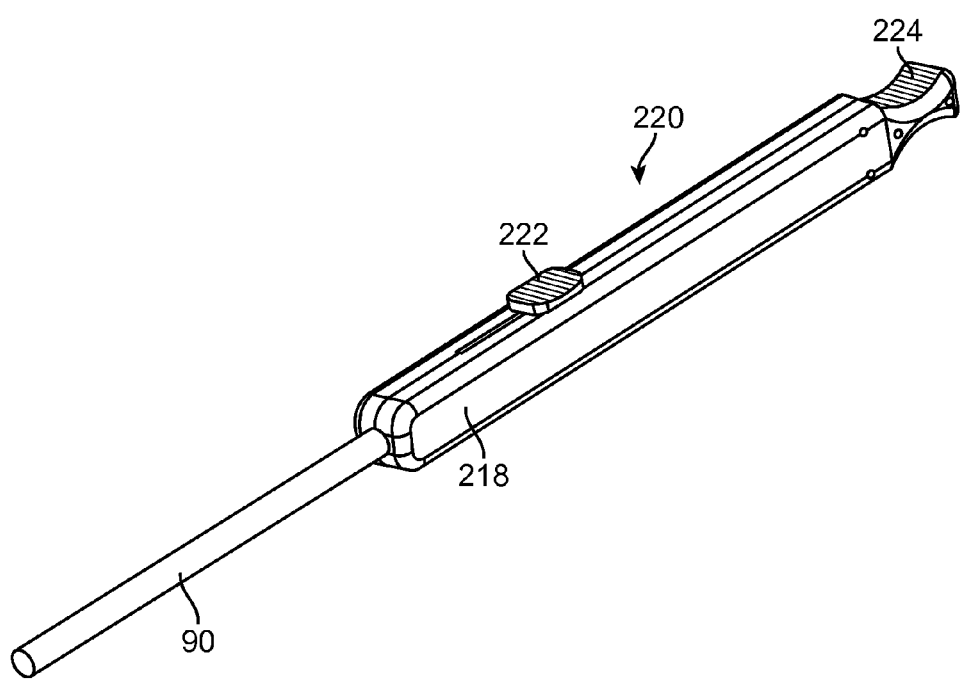
FIGS. 12A-12D illustrate aspects of a proximal deployment interface which may be utilized with closure device deployment configurations such as those depicted in FIGS. 9A-9E.
Figure 12B:
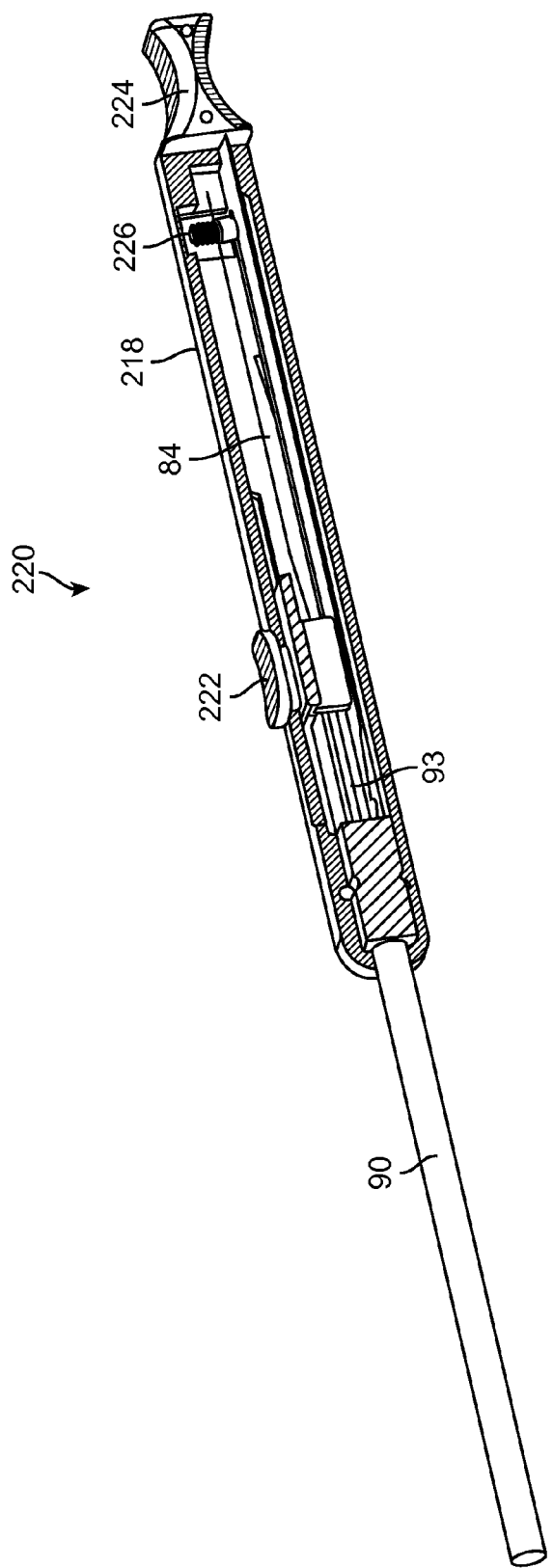
Figure 12C:
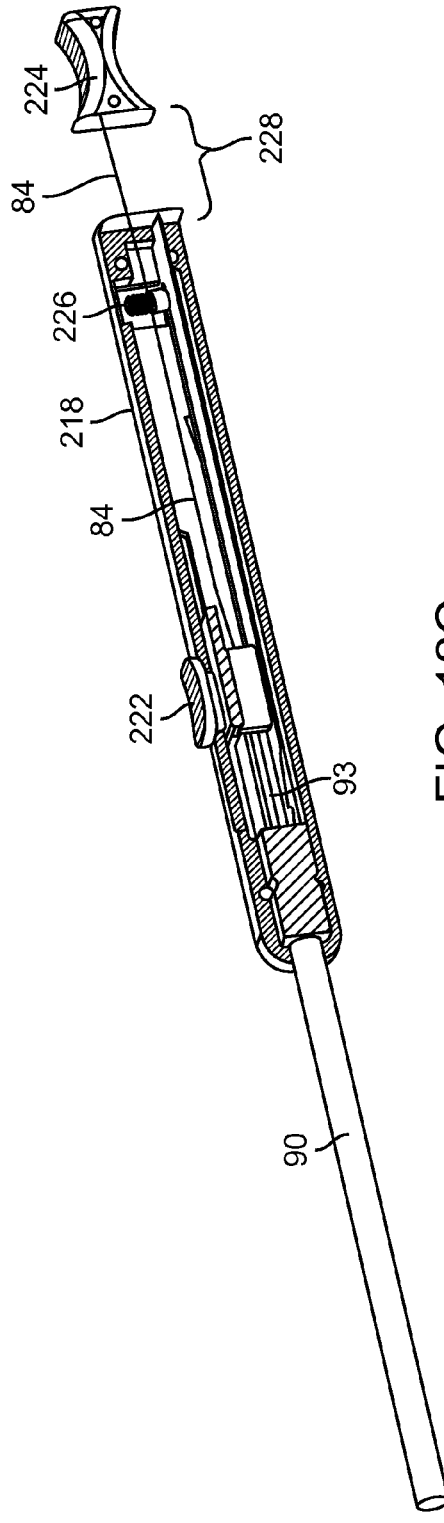
Figure 12D:
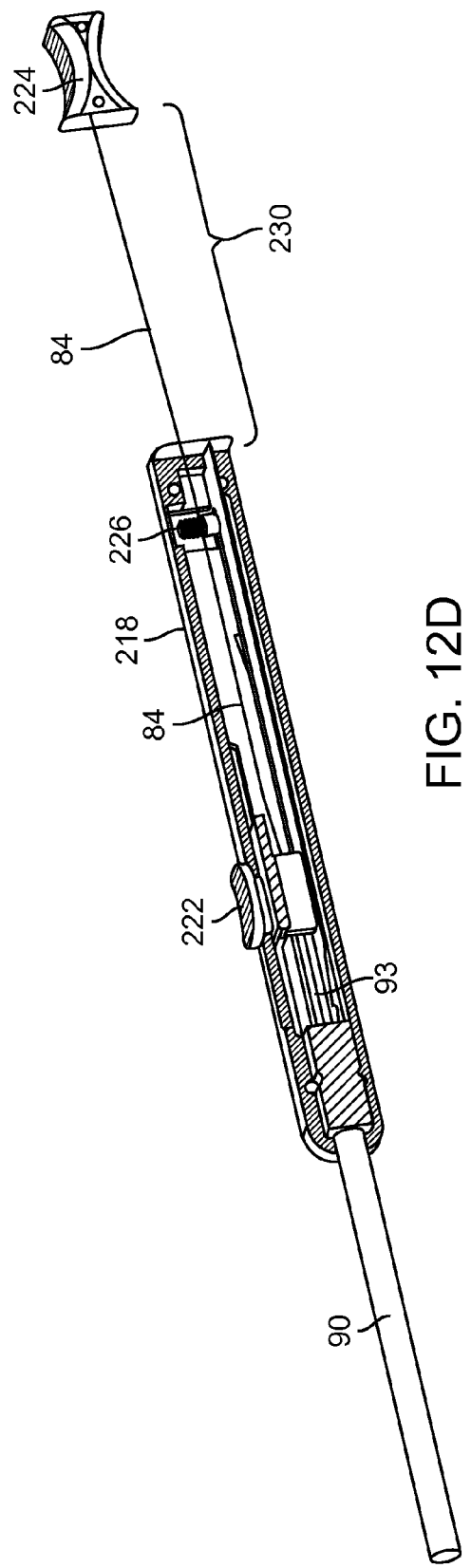

Referring to FIGS. 12A-12D, various aspects of a manual interface or control handle assembly for operating a closure device deployment system, such as those described in reference to FIGS. 6A-6X and 9A-9E, are illustrated. Referring to FIG. 12A, in one embodiment the control handle assembly (220) comprising a manipulable handle housing (218) and two manually movable elements (222, 224) configured to assist with various aspects of the deployment, is coupled to an elongate deployment member (90). Referring to the partial cutaway view of FIG. 12B, a foot member (93) extends distally through the elongate deployment member (90) and proximally is coupled to the first manually movable element (222), which is slidably coupled to the handle housing (218) to facilitate convenient thumb or finger insertion/retraction of the foot member (93) relative to the elongate deployment member (90). Extending proximally from the foot member (93), an attachment tension member (84) is coupled to a second manually movable element (224) by way of a spring-loaded mechanical fitting (226) configured to provide the operator with a tactile bump in tensile pull (using, for example, a small enlargement in the tension member that passes a fitting within the spring-loaded mechanical fitting) when he is about to release the attachment tension member from the housing, such that it may be left in situ. In operation, when the second movable element (224) is pulled proximally by a small amount (228) as in FIG. 12C, the movable element (224) detaches from the housing. Additional proximal pulling (230) takes the attachment tension member (84) past the detent, bump, or pull limit tactile feedback mechanism, to provide the operator with an understanding that pulling past such point permanently releases the attachment tension member (84) from the housing (84) and the control handle assembly (220) in general.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject interventions may be provided in packaged combination for use in executing such interventions. These supply "kits" further may include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally know or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

The invention claimed is:

1. A method of closing an opening in the wall of a blood vessel comprising:
    introducing a deployment assembly through an introducer into the opening, wherein the deployment assembly comprises a restraining member, a foot member, a collapsed closure device removably coupled to a distal end of the foot member, and a control member which passes through said foot member and is attached to said closure device;
    retracting the restraining member, thereby exposing the distal end of the foot member;
    activating said control member thereby controllably causing the foot member to flex, and thereby causing the closure device removably coupled thereto, to rotate within the blood vessel to a rotated orientation;
    decoupling the closure device from the distal end of the foot member, wherein at least a portion of the closure device is positioned adjacent to the opening; and
    retracting the deployment assembly.

2. The method of claim 1, wherein the closure device is removably coupled to the foot member with a first tether.

3. The method of claim 2, further comprising tensioning the first tether to urge the closure device against the vessel wall adjacent the opening.

4. The method of claim 2 wherein said first tether is looped around the closure device and is provided with a restraining knot.

5. The method of claim 4, comprising decoupling the closure device from the foot member by pulling the first tether in a proximal direction.

6. The method of claim 5, wherein pulling the first tether unties a restraining knot.

7. The method of claim 6, wherein the restraining knot is a highwayman's hitch.

8. The method of claim 1, wherein said foot member is provided with a crease to create a bending axis.

9. The method of claim 1, wherein said control member is a second tether, and further comprising applying a tensile load to said second tether to flex said foot member and to move the closure device to the rotated orientation.

10. The method of claim 1, wherein the restraining member comprises an elongate sheath.

11. The method of claim 1, further comprising leaving behind the closure device and the control member after withdrawing the deployment assembly.

12. The method of claim 1, wherein the closure device has a proximal end, a distal end, and a longitudinal length therebetween, the distal end being inserted most distally past the opening in the blood vessel, wherein the method further comprises positioning a portion of the closure device that lies in between the proximal and distal ends of the closure device against the opening in the blood vessel after rotating the closure device to the rotated orientation.

13. The method of claim 12, wherein the longitudinal length of the closure device is larger than a diameter of the opening in the blood vessel, such that after rotating the closure device to the rotated orientation, the closure device is geometrically prevented from exiting the opening.

14. The method of claim 1 wherein the control member is bioabsorbable.

15. A method of closing an opening in the wall of a blood vessel comprising:
    introducing a deployment assembly through an introducer into the opening, wherein the deployment assembly comprises a restraining member, a foot member which is restrained by said restraining member and which is pre-biased to flex when not restrained by said restraining member, a collapsed closure device removably coupled to a distal end of the foot member and a control member which passes through said foot member and is attached to said closure device;
    retracting the restraining member, thereby exposing the distal end of the foot member thereby allowing the foot member to flex and activating said control member thereby controllably assisting said foot member to flex, and thereby causing the closure device removably coupled thereto, to rotate within the blood vessel to a rotated orientation;
    decoupling the closure device from the distal end of the foot member, wherein at least a portion of the closure device is positioned adjacent to the opening; and
    retracting the deployment assembly.

16. The method of claim 15, wherein said foot member is removably coupled to said closure device by a first tether.

17. The method of claim 16, further comprising tensioning the first tether to urge the closure device against the vessel wall adjacent the opening.

18. The method of claim 16, comprising decoupling the closure device from the foot member by pulling the first tether in a proximal direction.

19. The method of claim 18 wherein pulling the first tether element unties a restraining knot.

20. The method of claim 19, wherein the restraining knot is a highwayman's hitch.

21. The method of claim 15 wherein said control member is a second tether and further comprising applying a tensile load to said second tether to assist in flexing said foot member and in moving the closure device to the rotated orientation.

22. The method of claim 15, wherein the restraining member comprises an elongate sheath.

23. The method of claim 15, wherein the closure device has a proximal end, a distal end, and a longitudinal length therebetween, the distal end being inserted most distally past the opening in the blood vessel, wherein the method further comprises positioning a portion of the closure device that lies in between the proximal and distal ends of the closure device against the opening in the blood vessel after rotating the closure device to the rotated orientation.

24. The method of claim 23, wherein the longitudinal length of the closure device is larger than a diameter of the opening in the blood vessel, such that after rotating the closure device to the rotated orientation, the closure device is geometrically prevented from exiting the opening.

25. The method of claim 15, further comprising leaving behind the closure device and the control member after withdrawing the deployment assembly.

26. The method of claim 15 wherein the control member is bioabsorbable.

* * * * *